US012740844B2

(12) United States Patent
Beck

(10) Patent No.: US 12,740,844 B2
(45) Date of Patent: Sep. 22, 2026

(54) VISUAL ALERT SYSTEM FOR USE WITH SAFETY BARRIERS AND METHODS OF MAKING THE SAME

(71) Applicant: BioBarrier, Inc., Laguna Nigel, CA (US)

(72) Inventor: Robin Thill Beck, Laguna Niguel, CA (US)

(73) Assignee: BioBarrier, Inc., Laguna Niguel, CA (US)

( * ) Notice: Subject to any disclaimer, the term of this patent is extended or adjusted under 35 U.S.C. 154(b) by 2189 days.

(21) Appl. No.: 16/308,662

(22) PCT Filed: Jun. 13, 2017

(86) PCT No.: PCT/US2017/037325
§ 371 (c)(1),
(2) Date: Dec. 10, 2018

(87) PCT Pub. No.: WO2017/218588
PCT Pub. Date: Dec. 21, 2017

(65) Prior Publication Data
US 2019/0254765 A1 Aug. 22, 2019

Related U.S. Application Data

(60) Provisional application No. 62/392,814, filed on Jun. 13, 2016.

(51) Int. Cl.
*A61B 42/30* (2016.01)
*A41D 19/00* (2006.01)
(Continued)

(52) U.S. Cl.
CPC .......... *A61B 42/10* (2016.02); *A41D 19/0006* (2013.01); *A41D 19/0031* (2013.01);
(Continued)

(58) Field of Classification Search
CPC . A61B 42/10; A61B 42/30; A61B 2090/0809; A41D 19/0006
See application file for complete search history.

(56) References Cited

U.S. PATENT DOCUMENTS 3,633,216 A * 1/1972 Schonholtz ........ A41D 19/0096 2/168
3,636,316 A 1/1972 Suzuki et al.
(Continued)

FOREIGN PATENT DOCUMENTS

AU 2010201191 A1 11/2010
WO WO-8905449 A * 6/1989
(Continued)

OTHER PUBLICATIONS

ISA/US, International Search Report for PCT/US2017/037325 Nov. 6, 2017 (4pgs.) and written opinion (10pgs.).
"Crystal Violet," Wikipedia.org.

*Primary Examiner* — Tajash D Patel
(74) *Attorney, Agent, or Firm* — BLAIR WALKER IP SERVICES, LLC

(57) ABSTRACT

A safety barrier for protecting a covered surface from exposure to dangerous fluids is provided with a membrane with a protected region having one or more built-in safety features defined by set of safety related properties and placed over the surface to inhibit the exposure of the dangerous fluids onto or into the surface and a safety indicator providing a visually perceptible alert at the outermost surface of the membrane indicative of at least one safety related property.

73 Claims, 17 Drawing Sheets

(51) Int. Cl.

| | |
|---|---|
| ***A41D 19/015*** | (2006.01) |
| ***A61B 42/10*** | (2016.01) |
| ***A61F 6/04*** | (2006.01) |
| ***B29D 99/00*** | (2010.01) |
| *A41D 31/30* | (2019.01) |
| *A61B 90/00* | (2016.01) |
| *B29K 7/00* | (2006.01) |

(52) U.S. Cl.

CPC ....... *A41D 19/015* (2013.01); *A41D 19/0157* (2013.01); *A61B 42/30* (2016.02); *A61F 6/04* (2013.01); *B29D 99/0067* (2013.01); *A41D 31/305* (2019.02); *A41D 2500/50* (2013.01); *A61B 2090/0809* (2016.02); *B29K 2007/00* (2013.01)

(56) References Cited

U.S. PATENT DOCUMENTS

| | | | | |
|---|---|---|---|---|
| 4,742,578 | A | | 5/1988 | Seid |
| 4,771,482 | A | | 9/1988 | Shlenker |
| 4,910,803 | A | | 3/1990 | Cukier |
| 4,919,966 | A | | 4/1990 | Shlenker |
| 4,935,260 | A | | 6/1990 | Shlenker |
| 5,045,341 | A | | 9/1991 | Shlenker |
| 5,073,365 | A | | 12/1991 | Katz et al. |
| 5,126,146 | A | | 6/1992 | Seminoff et al. |
| 5,128,168 | A | | 7/1992 | Shlenker et al. |
| 5,130,159 | A | | 7/1992 | Shlenker et al. |
| 5,182,142 | A | | 1/1993 | Hart et al. |
| 5,224,221 | A | | 7/1993 | Richardson et al. |
| 5,224,422 | A | | 7/1993 | Marozzi et al. |
| 5,304,375 | A | | 4/1994 | Marquardt et al. |
| 5,335,373 | A | | 8/1994 | Dangman et al. |
| 5,338,565 | A | | 8/1994 | Shlenker et al. |
| 5,357,636 | A | | 10/1994 | Dresdner, Jr. et al. |
| 5,421,033 | A | | 6/1995 | DeLeo |
| 5,428,841 | A | | 7/1995 | Stein |
| 5,483,697 | A | | 1/1996 | Fuchs |
| 5,549,924 | A | | 8/1996 | Shlenker et al. |
| 5,619,752 | A | * | 4/1997 | Haber .................... A61B 42/10 2/161.7 |
| 5,679,699 | A | | 10/1997 | Kehrbach et al. |
| 5,704,065 | A | | 1/1998 | Feuerhake |
| 5,811,471 | A | | 9/1998 | Shanbrom |
| 5,911,848 | A | * | 6/1999 | Haber .................... A61B 42/00 2/161.7 |
| 6,060,986 | A | * | 5/2000 | Lederer .................. A61B 42/30 340/604 |
| 6,145,130 | A | * | 11/2000 | Haber .................... A61B 42/30 2/161.7 |
| 6,175,962 | B1 | * | 1/2001 | Michelson ......... A41D 19/0058 2/161.7 |
| 6,183,764 | B1 | | 2/2001 | Shanbrom |
| 6,361,786 | B1 | | 3/2002 | Shanbrom |
| 6,365,278 | B1 | | 4/2002 | Hoerner et al. |
| 6,618,861 | B2 | | 9/2003 | Saks et al. |
| 6,807,681 | B2 | | 10/2004 | Sorrels |
| 7,300,770 | B2 | | 11/2007 | Martin et al. |
| 2001/0018095 | A1 | | 8/2001 | Shlenker et al. |
| 2003/0124354 | A1 | | 7/2003 | Vistins |
| 2006/0026737 | A1 | | 2/2006 | Chen |
| 2006/0059603 | A1 | | 3/2006 | Peng et al. |
| 2009/0070918 | A1 | | 3/2009 | Pickard et al. |
| 2011/0287553 | A1 | | 11/2011 | Hassan et al. |
| 2012/0135527 | A1 | | 5/2012 | Bangera et al. |
| 2013/0213094 | A1 | | 8/2013 | Moreland et al. |
| 2015/0189933 | A1 | | 7/2015 | Einesson |
| 2015/0362435 | A1 | | 12/2015 | Hassan et al. |
| 2016/0033418 | A1 | | 2/2016 | Eng et al. |

FOREIGN PATENT DOCUMENTS

| | | | | | |
|---|---|---|---|---|---|
| WO | WO-2017087797 | A1 | * | 5/2017 | ............. B32B 25/08 |
| WO | WO-2020076269 | A2 | * | 4/2020 | ............. A41D 31/04 |

* cited by examiner

Dry
(Step 1140)

Remove from
former
(Step 1142)

Chlorinate
(Step 1144)

Dry
(Step 1146)

Resultant
Product
(Step 1148)

FIG. 11C

*Dry*
*(Step 1240)*

*Remove from former*
*(Step 1242)*

*Chlorinate*
*(Step 1244)*

*Dry*
*(Step 1246)*

*Resultant Product*
*(Step 1248)*

| Property or Characteristic of Membrane Product (Built-in Advanced Safety Features): | | |
|---|---|---|
| **General Trait** | **Non-Limiting Available Specific Traits of Built-In Safety Features** | |
| Passive Feature Present | No | Yes |
| Active Feature Present | No | Yes |
| Passive Feature Location/Region | General | Specific |
| Active Feature Location/Region | General | Specific |
| Region Devoid of Feature | General | Specific |
| Multi-Feature | No | Yes |
| Reservoir Including Active Agent | No | Yes |
| Impregnated with Active Agent | No | Yes |
| Puncture Marking Feature | No | Yes |
| Other Characteristic Change | No | Yes |

1304

| **Specific Trait** | **Exemplary Protective Trait Details** | | |
|---|---|---|---|
| No. of layers | Single | Multi-Layer With Joined or Fused Sections | Multi-Layer With Discrete Separated Sections |
| Active Agent Type | Biocide | Anti-Microbial | Gentian Violet |
| Thickness | Less than 9 mil | 9-11 mil | Greater than 11 mil |
| Type of Material/Composition Change | Thickness | Hardness | Composition Change |
| Concentration Level of Active Agent | Low | Medium | High |

| Visual Alert Indicators | | | |
|---|---|---|---|
| Color | Tone | Number | Symbol |
| Pattern/Design | Line of Demarcation | Zone of Demarcation | Indicia |
| Text | Marking | Puncture Location Mark (Tattoo) | Imprint |
| Emboss | Dye | Pigment | Descriptor |
| Lines/Stripes | | | |

FIG. 14

VISUAL ALERT SYSTEM FOR USE WITH SAFETY BARRIERS AND METHODS OF MAKING THE SAME

CROSS REFERENCE TO RELATED APPLICATIONS

This application is a 371 of International Application No. PCT/US2017/037325 filed on Jun. 13, 2017 which claims the benefit of U.S. Application No. 62/392,814, filed on Jun. 13, 2016, entitled Multi-Colored Membrane Products and Method of Making the Same, and which is hereby incorporated by references in its entirety.

BACKGROUND

1. Field of the Invention

The present invention generally relates to protective barriers used to protect an underlying surface from exposure to dangerous fluids, and more particularly to, membrane products with passive and/or active safety features for donning to reduce the likelihood of exposing the wearer's skin to dangerous bodily fluids.

2. Background Art

Reduced exposure to dangerous fluids such as contagious, contaminated, life threatening, infectious, or other undesirable bodily fluids or hazardous chemicals, is of paramount concern to examiners, surgeons, and first responders. This concern often extends to persons outside such professions as well either in emergency or casual settings. To combat this exposure to such dangerous bodily fluids, a common solution is the donning of a glove or gloves, condoms, or other protective barrier to protect the wearer's skin, particularly prior to situations where bodily fluids may be present and there is the possibility that such fluids may be spread or exchanged. The same solution is typically used when handling objects where hazardous chemicals may be present as well.

With respect to gloves in particular, medical gloves are disposable gloves used during medical examinations and procedures that help prevent cross-contamination between caregivers and patients. Medical gloves may be made of different polymers, both natural and synthetic, including latex, nitrile rubber, polyvinyl chloride, and neoprene. They may come unpowdered, or powdered with cornstarch or other suitable powder to lubricate the gloves and make it easier to put the gloves on the user's hands. However this practice is less preferred with such powdering typically being applied prior to stripping the glove from the former. Alternatively, the glove may be chlorinated after being stripped from the former. Another alternative is the use of a hydrogel coating. Either approach makes the latex less tacky. Examination and surgical gloves are the two main types of medical gloves. Surgical gloves have more precise sizing with a better precision and sensitivity and are made to a higher standard. Examination gloves are available as either sterile or non-sterile, while surgical gloves are generally required to be sterile.

Historically, these gloves and other protective barrier products such as condoms are constructed of a single elastomeric membrane and simply provide a passive barrier protection to the wearer. These membranes are typically made from single layer of a natural material and, more recently, made from synthetic lattices or polymer-based materials. Such single layer membranes are especially vulnerable to puncture by sharp objects such as needles used in surgery, bone fragments, glass chips, metal fragments, and other puncturing, tearing, or slicing items, commonly referred to as "sharps". Such membranes are also subject, at times, to manufacturing defects such as pinholes and tears and can develop tears and openings during use. As such, these passive protective barriers are not a perfectly dependable barrier, especially for the user who can be exposed to infections and diseases from the patient or partner. Because pinholes and tears and sometimes even sharp punctures are not always visible or felt by the wearer, the wearer often continues the use of the product with no knowledge that the barrier on which he/she is relying has been severely compromised. One exemplary study regarding undiagnosed punctures may be found in *The Incidence of Undiagnosed Punctures in Non-Sterile Gloves* by Burke et al., published in the British Dental Journal (1990). This study provides the percentages of undiagnosed punctures ranging from 3-49% depending on glove type and 9-29% among practitioners. The location frequency of the undiagnosed punctures is also provided in the study with more than 60% of undiagnosed punctures in the thumbs and second fingers of the gloves. This may result in the exposure to dangerous fluids and may lead to infection, disease and even ultimately the loss of life. This also poses a risk to the patient or partner as infection has been shown to pass from the wearer to them.

One potential solution is described in U.S. Pat. No. 3,633,216 to Schonholtz in which a rubber surgical glove formed of a relatively thin material includes at least one reinforced region or cover about a finger portion to reduce the likelihood of complete penetration through the reinforced region by a needle. If desired, the cover may be provided in a color contrasting to that of the glove body. In addition, the cover is slightly larger than the underlying digit member, thus providing a clearance space therebetween which is filled with any conventional indicator substance such as colored saline solution. If the cover is ruptured or pierced, the indicator will leak through the resultant opening and contrastingly color the exterior of the cover so that a surgeon will immediately be made aware that a breach of the outer cover layer of the glove has been made and the glove must be discarded and replaced. The substance may also be a conventional antibacterial substance such as hexachlorophene or an iodophor or may be an indicator combined with such a substance if desired. According to the patent, the emission of the powder will occur before puncture of the inner glove portion, hence there will be adequate warning to change gloves. Thus, such solution provides a reinforced region about a thumb or index finger portion of a glove, which is a passive barrier protection feature, and provides a colored saline solution indication of a breach of the outer surface in the finger region only. However, Schonholtz does not provide an indication of a breach of the outermost surfaces in other regions of the glove or a breach at the innermost surface anywhere throughout the glove or provide an indication as to the specific type of protection.

Another potential response to the passive protection single layer glove is the double gloving option wherein a user slips a second glove over a first glove to offer two layers of protection. However, the difficulty of donning and removing the gloves makes this less than a desirable solution, especially in a surgery setting wherein the surgeon is using surgical gloves. The double gloving option also offers less sensitivity and is not preferred by many surgeons.

Several other important breakthroughs advancing beyond this single layer, passive barrier protection technology and/ or double gloving practice were made in the late 1980s and into the 1990s. Starting with U.S. Pat. No. 4,771,482 to Shlenker (the same inventor listed in the this application), and continuing with U.S. Pat. Nos. 4,919,966; 4,935,260; 5,045,341; 5,128,168; 5,130,159; 5,165,593; 5,338,565; 5,549,924; 5,679,399; and 5,965,276, all to Shlenker, which are all incorporated by referenced herein, a series of breakthroughs involving the prevention of cross-contaminating bodily fluids onto or into the surface of the wearer's skin were developed. In general, these improvements to these passive film barriers were implemented by the addition of"active agents" such as biocides and an anti-microbial substances either integrated into the matrix of the membrane layers of the gloves or stored in reservoirs in or between layers. Related improvements included the addition of one or more discrete layers to the single film membrane, providing the feel of a single layer glove while also providing the advanced protection of the double gloving practice. These added film layers and "active agents" are incorporated into medical gloves to help to wipe oft and or disinfect, harmful substances carried on needlesticks and other sharp objects that may puncture medical gloves while in use. These improvements have been proven to lessen the transfer of HIV virus and several types of bacteria.

While such advances aim at reducing the likelihood of bodily fluid contamination, such devices generally do not provide a visual indicator or indication system to identify the presence of these new additional barriers and or "active" agents, where such features are incorporated, as well as the specific type of features as compared to other conventional continuous, uniformly colored elastomer membrane products, or how these advanced protective membrane products differ from one another as to their beneficial features.

Such visual indicators would be beneficial since clinicians often do not read the glove package and/or the gloves have been removed from the package. Thus, when the gloves are only one color, the surgeon or the nurse cannot immediately recognize whether the glove is in fact a multilayered glove or whether the glove has pinhole leaks or other defects. In addition, a visual indicator system that provides practically instant recognition would be advantageous given the criticality of time and amount of decision making that takes places, especially in life threatening situations.

One potential approach may be found in U.S. Pat. No. 8,104,097 to Hamann. In general, Hamann discloses a multilayer glove in which the outside layer of the article is a different color relative to the inside layer or wearer contacting surface of the article so that the user of the article can readily identify the article as a multilayer elastomeric article. However, Hamann requires the user to visually inspect both the exterior and interior surfaces of the glove to determine a difference that leads to a conclusion of a multi-layer product. Given that the interior surface may not be readily discernible in poor lighting situations, this approach has its drawbacks. In addition, there is a time element inherent in manipulating and examining both surfaces of the glove to make such a determination. The Hamann solution does not allow the user to simply identify the multiple layer characteristics as the product is withdrawn from the packaging either. In addition, Hamann is restricted to multi-layer glove constructions and is silent regarding the provision of a visual alert identifying the presence, specific location, or type of any built-in safety features such as a biocide or anti-microbial substance.

Another potential approach may be found in U.S. Patent Application Publication No. US 2003/0124354 to Vistins. In Vistins, a glove is described that can be manufactured to visually signal a user that it includes multiple layers, imparting the knowledge that multiple layers of barrier protection are present on the glove. This is generally accomplished by varying the colors of the inner and outer layers, similar to the Hamann approach, and rendering one layer more translucent or transparent to view the other layer. The user of the glove or other film-based article can visually observe the multiple layers of the article from the outside or the inside of the glove, as an indicator of the increased level of passive barrier protection. However, Vistins merely provides a color indication that multiple layers may be present but does not address the presence of active agents, the specific location of additional safety protections, or the specific type of advanced protection with regards to active agents such as biocides, anti-microbial substances, or anti-bacterial substances that would alert a user to the location and type of protection.

Even with the inclusion of more active protection features versus simple passive protections, such membrane products may also benefit from a way to visually depict on the wearer's skin where a sharp either touched or penetrated the skin. One approach may be found in U.S. Pat. No. 5,459,879 to Fuchs. Fuchs discloses a multi-layer glove with a liquid solution including a dye disposed between inner and outer layers of the glove for a visual indication of punctures or tears in the outer layer. However, if the glove is punctured completely through, the user's hand may be stained by the dye once the sharp is removed and the liquid dye leaks or seeps through the tear left by the sharp object. The dye may include a bactericide and require alcohol to remove. However, it worth noting that the liquid dye does not adhere to the sharp and instead moves out of the way as the sharp penetrates the layers of the glove. Instead, the dye must seep or leak back into the tear created by the sharp to disperse on the skin near the hole. Such approach may have some advantages but also has several drawbacks. The liquid dye does not accompany the sharp and therefore may not accurately reflect the entry point since the glove layers and rupture may slide around as the sharp is withdrawn. This would cause the dye to leak through the hole and stain the wrong area of the underlying skin, especially as the glove is being removed. The dye may also smear and indicate a much larger area than necessary. In addition, the dye is easily wiped off and may simply be removed due to the sweat or other bodily fluids between the glove and the user's skin prior to removing the glove to see the stain. Thus, there are both significant accuracy and reliability issues with the Fuchs approach.

While the foregoing product solutions may perform well under certain conditions, what is needed is a protective barrier with built-in advanced protection safety features that are accompanied by a visual alert system allowing a user to rapidly identify and distinguish the presence, location, and/or type of one or more safety features relative to both more passive protection based products and/or products with a different sets of advanced features and/or alert the user to one or more instances of contact with a sharp object through the innermost layer of the barrier.

SUMMARY

In general, the present invention and exemplary embodiments thereof introduce membranes and membrane products that incorporate different colors, dyes and markings to indicate the presence of particular and useful features. It is particularly directed to protective elastomer membrane products such as gloves and condoms that incorporate different colors, dyes and or markings to indicate the presence of "active agents" (defined below) and or additional layers of protective membranes and to indicate, by transfer of the colorants or dyes onto or into the skin of the wearer, (a "tattooing effect"), an injury inflicted by a sharp object, possibly carrying harmful pathogens, upon the skin, during the course of use, and methods for making the same.

In at least one embodiment constructed in accordance with the principles of the present invention, the advanced glove membrane product incorporates a visually perceptible alert system with one or more visual indicators including colors, symbols, markings, indicia, patterns, numbers, or demarcated regions, or a combination thereof, on the surface of these advanced glove membrane product and affords the user a way to rapidly distinguish, by viewing the visual indicators, between a more protective "active agent" multi-layer glove and the less protective "passive" barrier single-layer glove. For instance, in the medical glove field, studies have shown that the wearer is usually most at risk from needle-stick injuries in the finger and palm portion of the glove. The visual indicators may depict the presence and exact location of these additional protective features and signal the advanced protection such a product could provide. The means by which to make this choice in a timely fashion could prove critical in instances of sharps' injuries and or breaches in the glove product.

In at least one embodiment constructed in accordance with the principles of the present invention, the visual indicator identifies and quickly conveys to the user the exact type of protective features the associated glove contains. This is important, especially in a harried situation such as on a battlefield, in an emergency room, or at the site of an accident, so that the user may rapidly identify which glove or glove pair would best suit the type of situation at hand and offer the best protection for the wearer of this glove in this situation.

In at least one embodiment constructed in accordance with the principles of the present invention, an additional benefit of incorporating a color and/or dye into the glove to provide a visual alert to show the presence of an "active agent" is that, should a sharp object, carrying infectious material that can cause infection and or life-threatening diseases, penetrate the innermost surface of the product membrane (i.e., the last line of defense before the skin) and pierce the skin, some of the colorant or dye is able attach to the sharp and be carried into the skin of the wearer. Such effect pin-points, by a visual tattoo effect, where that puncture of skin occurred. Because literature shows sharps' punctures can be so slight as to sometimes not be felt at all, this dye transfer tattooing effect onto the skin would enable the wearer to see, once the gloves are removed, the instance of an actual injury and consequently that he or she may need to report the accident and be given the proper prophylactic medicine in a timely manner. And the carry-over of the "active agent" into the skin on the object may help neutralize the infectious agent in the skin and lead to a healthier outcome. Also, a person may feel a needlestick injury but be unable to find the actual puncture site and waste valuable time in searching for the site of the injury in order to treat the injured area. The visible evidence of skin puncture by color imprint and the locations of such punctures would also inform and advance on-going studies to further the design of more protective medical products and to develop safer surgical techniques.

In accordance with the principles of the present invention, a safety barrier for protecting an underlying surface from exposure to dangerous fluids may be provided with a membrane having a form constructed to closely conform with the underlying surface and having an outermost surface disposed distalmost from the underlying surface when in a covering position and at least one region with one or more built-in safety features and a corresponding safety alert or visual indicator element that is visually perceptible at or through the outermost surface of the membrane to rapidly alert the wearer to the presence of at least one advanced active protection feature as compared to a conventional, passive protection, uniform color glove.

At least one exemplary embodiment constructed in accordance with the principles of the present invention provides either single and multi-layer elastomer membrane products that are bi-color, tri-color, or otherwise multi-colored surfaces and or have multiple tones of colors to provide a visual alert indicating the distinct features of the products. Such membrane products may exhibit a particular color or colors to indicate the location of an active agent (e.g., an active antimicrobial or indicating agent) and or to indicate an additional protective layer to the product and to indicate a change or difference in the features and or in the level of protection and or the number of layers and types of barrier capabilities along the body of the membrane, including a reservoir feature and or to indicate a change in thickness and or a change in material and or characteristic.

According to another embodiment constructed in accordance with the principles of the present invention, a membrane product may have a visual alert in the form of a double stripe of a color to indicate the higher level of safety provided by a double layer. Further, specific colors may be used to identify specific "active agents" in a membrane product. According to another embodiment of the present invention, a portion of a membrane product may be a particular color to indicate an agent in such colored portion. In another embodiment, a portion of a membrane product may be a particular color to indicate a certain number of membrane layers present at such colored portion. Further, a demarcation line or zone between different colors may mark where the product contains the active agent and where it is devoid of the active agent, where the membrane product has a different number of membrane layers, where a change in the construction of the membrane product is located, as well as other different beneficial characteristics.

Another embodiment constructed in accordance with the principles of the present invention may provide a visual alert or indicator by imprinting or embossing or otherwise marking indicia such as a number, a design, a pattern, a symbol, or a descriptor onto or into the product membrane during the manufacturing process on an inner and or outer membrane layer and that membrane layer may be in conjunction with a transparent or translucent later so that the marking is visible there through indicating that the product features a change in features, protection level and or its construction.

In one aspect of the present invention the different latex and active film layers may be admixed with one or more colorants to provide a visual indication to a user of the differently protected layers of the glove. Alternatively, the different latex and antimicrobial film layers may be colored with the same colorant, but having a degree of translucency such that multiple overlying layers produces a different resulting outer color perceived by a user. As one example, the finger and thumb portions may have a dark purple color to indicate maximum protection, the palm region may have a lighter purple or lavender color to indicate an intermediate degree of protection, and the cuff portion may have a white color to indicate a lower degree of protection.

Another embodiment constructed in accordance with the principles of the present invention may include the addition of dyes that make it possible for the wearer to have a dye imprint on his or her skin where it has been injured by a sharp object that has passed through the product and into their clothing and or skin in the normal course of use.

Methods of making such membrane products with visual alert systems are also disclosed herein.

All of the embodiments summarized above are intended to be within the scope of the invention herein disclosed. However, despite the discussion of certain embodiments herein, only the appended claims (and not the present summary) are intended to define the invention. The summarized embodiments, and other embodiments and aspects of the present invention, will become readily apparent to those skilled in the art from the following detailed description of the preferred embodiments having reference to the attached figures, the invention not being limited to any particular embodiment(s) disclosed.

BRIEF DESCRIPTION OF THE DRAWINGS

The accompanying drawings, which are incorporated herein form a part of the specification, illustrate certain exemplary embodiments of the present invention and, together with the description, further serve to explain the principles of the invention and to enable a person skilled in the pertinent art to make and use the invention.

As an initial note, these

FIG. 1A is a top plan view of an exemplary membrane product constructed in accordance with the principles of the present invention in the form of a left-handed glove in a palm down orientation, with a finger region, a palm region, a cuff region, and a visual alert system indicative of a set of built-in safety features present in the membrane product, the right handed view with palm up orientation being a mirror image thereof.

FIG. 2A is a similar view to FIG. 1 of another exemplary membrane product in the form of a glove and illustrating a variation of the visual alert system indicative of a set of built-in safety features.

FIG. 3A is a similar view to FIG. 1 of another exemplary membrane product in the form of a glove and illustrating another variation of the visual alert system indicative of a set of built-in safety features.

FIG. 4 is a similar view to FIG. 1 depicting another exemplary membrane product in the form of a glove and illustrating a variation of the visual alert system indicative of a set of built-in safety features.

FIG. 5 is a similar view to FIG. 1 depicting of another exemplary membrane product in the form of a glove and illustrating a variation of the visual alert system indicative of a set of built-in safety features.

FIG. 6 is a similar view to FIG. 1 depicting another exemplary membrane product in the form of a glove and illustrating a variation of the visual alert system indicative of a set of built-in safety features.

FIG. 7 is a similar view to FIG. 1 depicting another exemplary membrane product in the form of a glove and illustrating a variation of the visual alert system indicative of a set of built-in safety features.

FIG. 8A is a similar view to FIG. 1 depicting of another exemplary membrane product in the form of a glove and illustrating a variation of the visual alert system indicative of a set of built-in safety features.

Figure 11C:
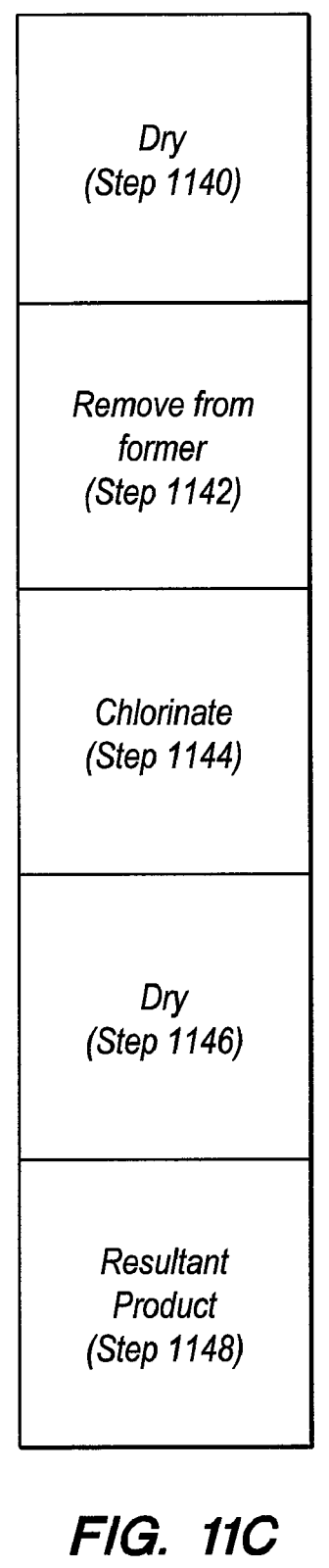

FIGS. 11A-C is an exemplary process for constructing a membrane product, such as a glove, with multi-colored active or non-active membranes and including imprint features, and/or dye transfer tattooing features. in accordance with the principles of the present invention.

Figure 12C:
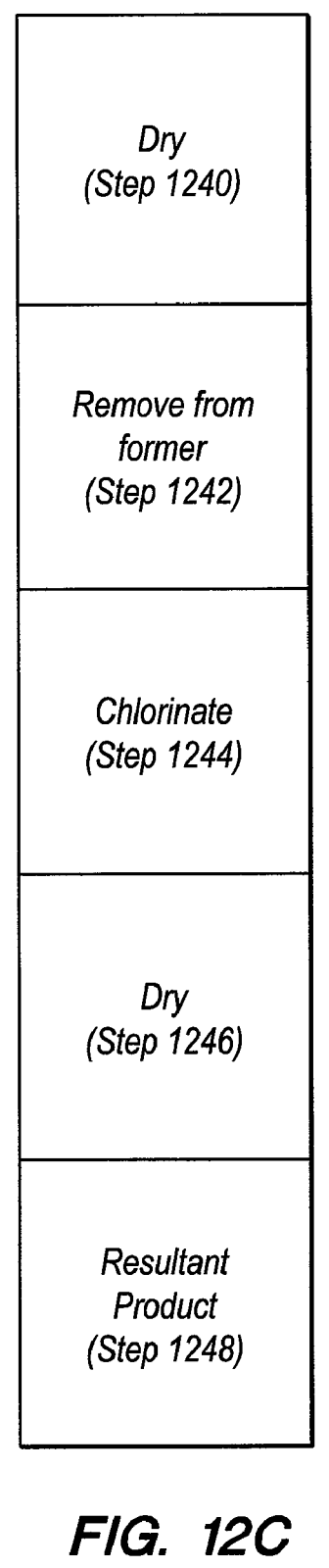

FIGS. 12A-C is an exemplary process for constructing a membrane product, such as a glove, with multi-colored membranes with one or more discrete layers and including an imprint feature and/or dye transfer (tattoo) feature in accordance with the principles of the present invention.

FIG. 13 is a matrix illustrating an exemplary set of advanced protection properties or built-in safety features and their respective general or specific traits that may be incorporated into or onto the surfaces or layers of the membrane products constructed in accordance with the principles of the present invention.

FIG. 14 is a matrix illustrating an exemplary set of visual alert indicators that may be used with the membrane products constructed in accordance with the principles of the present invention by indicating one or more built-in safety features.

DETAILED DESCRIPTION OF THE PREFERRED EMBODIMENTS

Figures 1A, 1B:
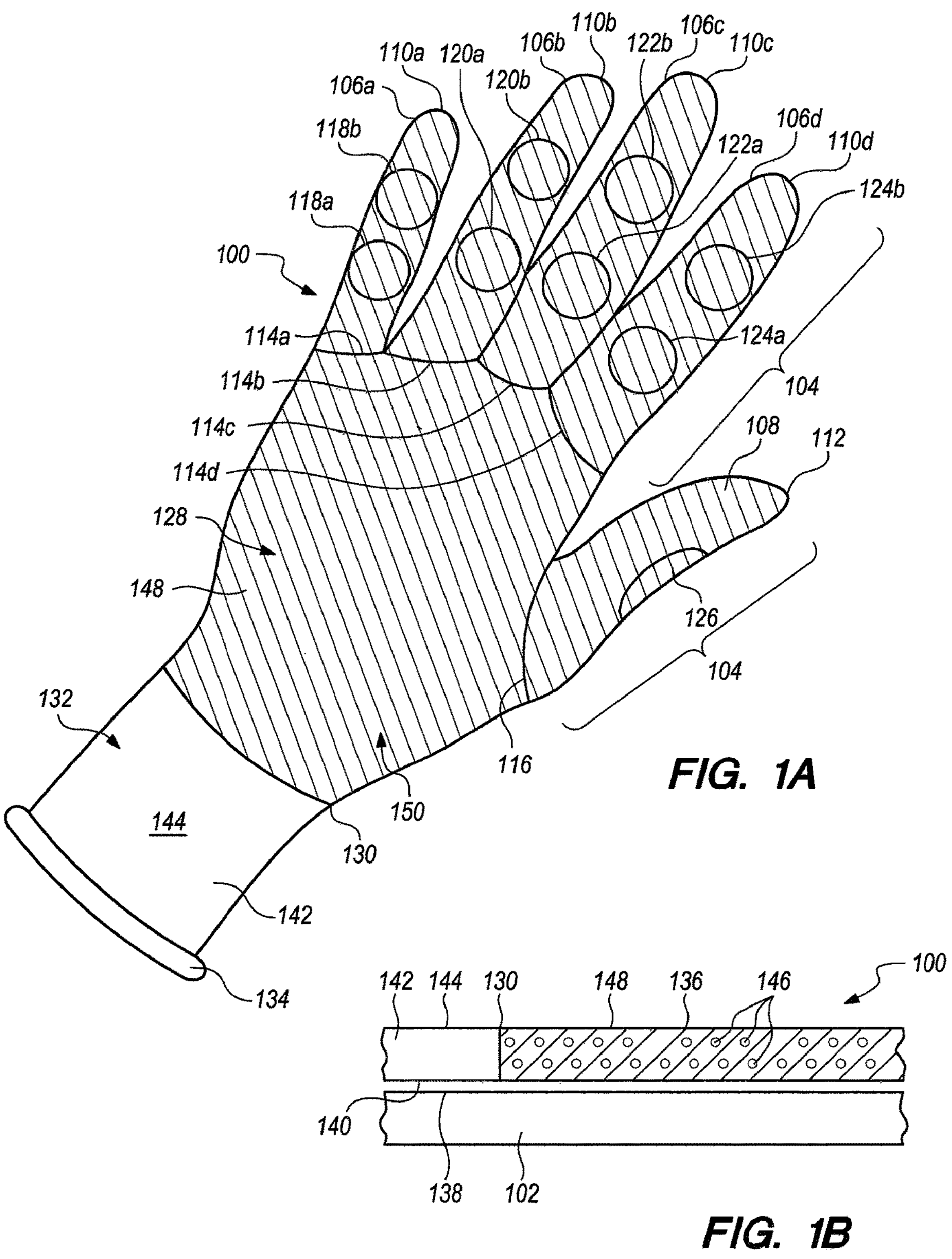
FIGS. 1A, 2A, 3A, 4, 5, 6, 7, and 8A depict a left handed, finished, stripped off straight product, that is, the first layer of film deposited on a former remains the inner layer of the finished product. However, in the further described manufacturing process, when layers are placed onto glove or condom formers and stripped off at the end of the dipping process they may either be stripped off straight as described above—or they may be stripped off inverted wherein the first layer of film deposited on a former becomes the outside layer of the finished glove or condom product. The sequence of manufacturing steps outlined below are for a stripped off straight end products but can be adjusted accordingly for a stripped off inverted end product as would be understood by one of ordinary skill in the art.
FIG. 1B is a cross sectional view taken from a portion of the glove in FIG. 1A illustrating a partial cutaway view of the palm and cuff regions.

With initial reference to FIGS. 1A-1B, an exemplary membrane product, generally designated 100 and constructed in accordance with the principles of the present invention, is illustrated. In this exemplary embodiment, such membrane product is generally provided in the form of a glove, such as an examination glove or a surgical glove, and constructed to fit closely over a wearer's hand, a portion of which is generally represented by reference numeral 102 in FIG. 1B. In this description, a membrane is a protective barrier, typically a thin pliable sheet or layer that acts as a passive boundary that is selective in nature as to what passes therethrough. In the exemplary embodiments described herein, the passive protection regions in the membranes may be used to prevent or inhibit dangerous fluids from contacting or penetrating the user's skin. However, such passive protection in the form of a simple barrier is enhanced by employing "active agents" in or between such barriers as will be described below.

Continuing with reference to FIG. 1A, the glove 100 includes a distalmost finger region 104 collectively comprised of four fingers 106*a-d* (pinky, ring, middle, index or pointer) and a thumb 108 running from their respective finger tips 110*a-d* and thumb tip 112 to the base of each respective digit 114*a-d* and 116. Within each discrete finger region 106*a-d* is a pair of knuckle regions 118*a-b*, 120*a-b*, 122*a-b*, and 124*a-b* respectively. The thumb region 106 includes a single knuckle region 126.

Adjacent the finger region 104 is a palm region, generally designated 128, projecting generally from the base of each digit 106*a-d* and 108 to the top of the wrist as indicated by the line of demarcation 130. A cuff region, generally designated 132, that extends from the line of demarcation 130 to cover a portion of the user's hand below the wrist and terminates at its innermost point (furthest from the finger tips 110*a-d* and 112) in a ring roll 134, which be considered part of the cuff region or a discrete component.

In this exemplary embodiment, referring now to FIG. 1B, the membrane product 100 is provided by a single layer membrane having an outermost surface 136 that is distalmost from a protected surface 138 such as the user's skin (epidermal surface) on the user's hand 102 and an innermost surface 140 that is more proximate to the protected surface 138 relative to the outermost surface and tends to abut the epidermal surface when the glove 100 is donned by the user.

Referring again to FIG. 1A as well as FIG. 1B, the membrane product 100 further includes a first region 142 coinciding in this exemplary embodiment with the cuff region 132 that includes a first color indicated by the unmarked area 144. In this exemplary embodiment, the first region 142 includes only passive protection in the form of a single layer of elastomeric protection as would be provided by a conventional single layer glove. Adjacent the cuff region 132 is the palm region 128 and beyond that the finger region 104. In this exemplary embodiment, both the palm region 128 and the finger region 104 cooperate to define an advanced protection region 150 (also referred to as protected region, active region, or active protected region) that includes an active agent 146 adding a built-in safety feature into the glove construction. Protected regions may include features other than an active agent however, as will be discussed below.

For purposes of this description, the term "active agent" refers to an agent that imparts an antimicrobial, biocide or disinfecting effect on pathogens that may come in contact with one or more layers or surfaces of the glove 100 and penetrate the glove material by either a puncture from a sharp object or by a breach in the glove material. An active agent may also be used for other activities such as providing a chemical indicator to visually display the presence of certain pathogens. One preferred agent for this embodiment is gentian violet as that agent acts as both a dye and has antimicrobial and anti-bacterial properties. The active agent, such as an antimicrobial or biocide, may be colored and or contain a dye resulting in a second colored region as indicated by the diagonal lines 148 in FIG. 1 to indicate the presence of the active agent. As will be described below, the active agent may be deposited on the elastomer dip or impregnated into the membrane during the manufacturing and may be added into or onto the entire glove or portions of the glove.

It will be appreciated that, in this exemplary embodiment, the first color 144, indicated by the unmarked area in the cuff region 132, is a different or otherwise contrasting color from that of the second color, indicated by diagonal lines 148 in the finger and palm regions, 104 and 128, respectively, collectively defining an advanced protection region 150. Alternatively, the contrast in color between the passive region 142 and the active region 150 may be provided by varying color tones or concentrations of color. In this exemplary embodiment, as explained in more detail below, the first color 144 is produced by dipping the glove all the way to the innermost end of the cuff region 132 while the different colored protected regions 104 and 128 (collectively, advanced protection region 150) are produced by dipping the glove during the manufacturing process up to only the cuff line 130. The different colored regions 144, 148, either alone or in conjunction with the cuff line 130 provide a visual alert as to the location of the passive protection (region 144) and the location of the active protection (region 150). The cuff line 130 also signifies a clear line of demarcation where one color stops and the other begins to visually indicate where the passive and active regions terminate. The cuff or ring roll 134 may be either a passive region or an active region as well.

The different colors 144, 148 (or tones of color) may be used to denote separate and distinct features of the membrane product 100 and cooperate to define a visual alert system with one more visual indicators indicative of one or more safety features present in the glove, particularly in comparison to a conventional, single layer, uniformly colored glove. Such visual alert system with one more visual indicators, as used throughout the embodiments described herein, and in accordance with the principles of the present invention, may be tailored according to the safety features to allow a user to quickly determine the presence, location, and specific types of built-in safety features available in the glove.

In this first embodiment, the cuff line 130 (or demarcation line) marks a clear border or terminus of at least one safety feature of the membrane product 100 present in protected region 150 such as double layer or presence of an active agent but absent in unprotected region 142. The demarcation line 130 may mark a border or terminus of a safety feature of membrane product 100 present in region 142 and also in region 150 but in a different composition. The color and tone of region 150 may or may not signify the presence of an active agent and or alternative composition of material in that region. The color and tone of region 150 may signify the same but different concentration of active agent in region 142 and or different variations of compositions than that of region 1420. The different colors of tones may denote separate and distinct features of the membrane product. The presence of such active agents or other components may begin at a fingertip region 110*a-d* and 112, carry through the palm region 128 and may terminate at demarcation line 130 at the top of the cuff region 132, extend throughout the entire glove, or appear in other regions of the gloves such as, but not limited to, the fingertips 110*a-d*, 112, knuckles regions 118*a*0*b*, 120*a-b*, 122*a-b*, 124*a-b*, and 126, top surface or undersurface (palm side) of the glove, finger or fingers, palm, cuff or other region suitable for providing the desired level of protection. The active and passive regions may be adjacent or spaced apart from one another. More than one active or passive region may be used and such regions may be adjacent or spaced apart as well. A portion of an active region overlapping a passive region would generally be considered an active region. In one embodiment, a demarcation 130 may mark a border or terminus of a feature of membrane product 100 present in region 142 but absent in region 150. Region 150 may contain any active agent, such as a biocide, anti-microbial substance, gentian violet, in the same or different concentration or a different biocide that is contained in region 142, if employed therein. A membrane layer or surface may be impregnated or coated with a biocide or other substances. Suitable biocides for use in membrane products according to the present invention include, for example, phenols, dyes, gentian and or crystal violet, chlorhexidine, triclosan, nonoxynol 9, benzalconium, betadine and silver salts.

With continuing reference to FIGS. 1A-1B, the glove product 100 may contain as well as a colorant to produce the differing colors and or tones of colors and also dyes that produce the different colors or tones of color and produce a dye transfer effect onto the wearer of the glove when a sharp object passes through it and into the wearer's skin and or clothing. Dyes and colorants that can transfer can be contained between layers of elastomers, deposited on elastomers, add-mixed into elastomers, add-mixed into coagulants, and act as coagulants themselves in the manufacturing process. This tattooing effect is described in more detail with reference to FIG. 9 below.

With continued reference to FIGS. 1A-1B, the glove product 100 outermost and innermost elastomer latex membranes 136, 140, respectively, may be of different thicknesses from each other and may be of different materials than each other and contain different actives. The elastomer latex layers and the active film antimicrobial may be formed by a dipping process or a spraying process using a conventional glove former. Alternatively, a combination of dipping and spraying may be employed.

Figures 2A, 2B:
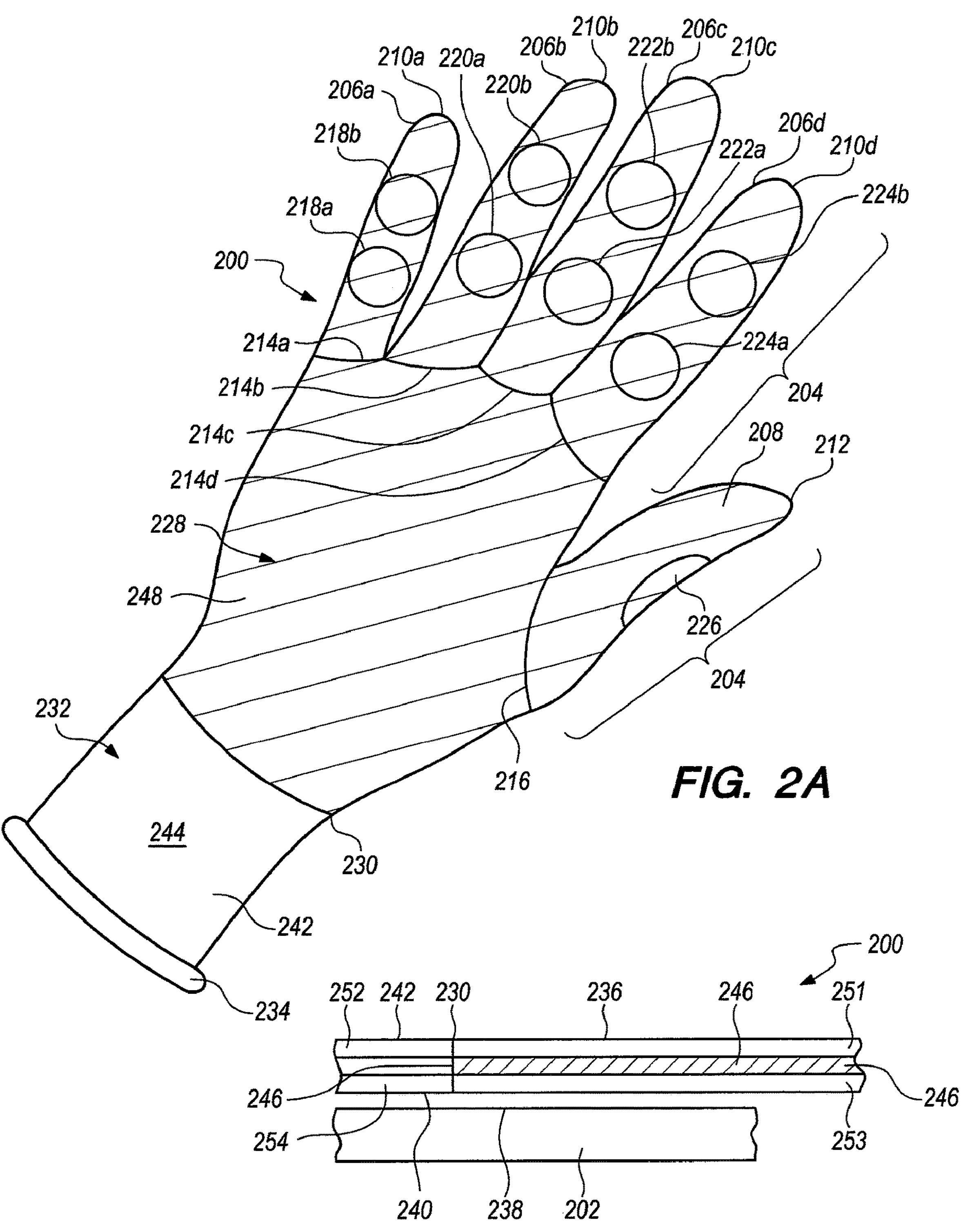
FIG. 2B is a cross sectional view taken from a portion of the glove in FIG. 2A illustrating a partial cutaway view of palm and cuff regions.

Referring now to FIGS. 2A-2B, wherein like components are numbered alike, another exemplary embodiment constructed in accordance with the principles of the present invention and generally designated 200 is shown. As with the prior embodiment, the product membrane 200 is in the form of a glove for covering a portion of a user's hand 202 and providing a visual alert system for rapidly identifying the protective features of the glove and distinguishing the glove 200 from other gloves with a different set of protective features. As with the prior embodiment in FIGS. 1A-1B, the glove 200 contains includes a distalmost finger region 204 including four finger extensions 206*a*-*d* and a thumb extension 208 with each finger extending from a respective fingertip 210*a*-*d* and a thumb tip 212 and terminating at the base of each digit 214*a*-*d*, respectively, and the base of the thumb 216. The pinky finger extension 206*a* includes lower and upper knuckle regions, 218*a*, 218*b*, respectively. Similarly, the ring finger extension 206*b* includes lower and upper knuckle regions 220*a*, 220*b*, respectively. The middle finger extension 206*c* also includes lower and upper knuckle regions, 222*a*, 222*b*, respectively. The index finger extension 206*d* includes similar lower and upper knuckle regions 224*a*, 224*b*, respectively, as well. Finally, the thumb extension 208 includes a single knuckle region 226.

The glove 200 further includes a palm region, generally designated 228, projecting from the base of each finger and thumb region 206*a*-*d* and 208 to a line of demarcation 230, which separates the palm region from a cuff region 232. At the innermost extent of the cuff region is a cuff or ring roll 234.

Referring now to FIG. 2B, the glove 200 is a dual layer integrated membrane with an outermost surface 236 and an innermost surface 240 for covering the wearer's skin 238. In addition, an active agent 246 is impregnated into the membrane or sandwiched between an outermost layer 252 and an innermost layer 254. As shown in FIG. 2B, the active agent 246 does not appear in the cuff region 232 but only in the palm region 228 and finger region 204. Moreover, the active agent is spaced inwardly from the outermost surface 236 and innermost surface 240 leaving an upper gap 251 (coinciding with the upper layer) and a lower gap 253 (coinciding with the lower layer) where the active agent is not present within the membrane as well. However, a sharp passing through the entire membrane from the outermost surface and into the active agent region 246 would encounter the active agent. This includes sharps passing through the innermost layer 240. The regions 251, 253 of the outer and inner layers of elastomer membrane that do not contain an active agent contrasts the appearance of the active agent region 246 and may for example, be any color indicated by the unmarked region 244 or non-color (e.g., translucent or transparent) other than the color in active agent region 246 indicated by the diagonal lines 248. Additionally, the color of the active agent may show through the layers of elastomer membrane to give the region 246 its final color.

Such glove 200 includes a visual alert or indicator in the form of a color contrast between adjacent regions to rapidly alert a use to presence of the active agent 246 as well. In this exemplary embodiment, the palm and finger regions 228, 232, respectively, define an advanced protection region 250 that includes a first color indicated by the diagonal lines 248 (as seen through the outermost layer 252 or innermost layer 254) to indicate the presence of the active agent 246 in the glove membrane while the cuff region 232 remains devoid of the active agent and is of a different color indicated than the unmarked area 244. Alternatively, instead of contrasting colors from a different region in the color spectrum, the contrast may be provided by a white and non-white color set in the respective regions or a paler version or darker version of the color in the other region.

During the manufacturing process, the first innermost layer 254 is dipped onto or otherwise deposited on the glove former from the bottom fingertip edge of the former to the top or cuff area 232 near the ring roll 234. An additional active agent layer 246 which may or may not contain an elastomer is deposited on the former over the innermost layer 252 from the bottom fingertip edge of the former in the region 250 to the point at cuff line 230. Then an additional layer (the outermost layer 252) of elastomer is deposited over region 250, past point 230 and through region 232 to the end of the cuff area. In the drying process these three layers will become a single membrane. Alternatively, the treated layers may separate into discrete layers.

It will be appreciated that the glove 200 includes an active agent region 250 contained in the area above the cuff denoted by a first color indicated by diagonal lines 248. Region 250 is adjacent to the bottom cuff area of the glove region 232 which is a second contrasting color, indicated by the unmarked area 244, which may be a natural, neutral, white or color other than the first color and does not contain the active agent. The unmarked passive region in contrast to the contrasting colored active agent region provides a visual indicator as the presence, location, and type of protection of the built-in safety feature in the form of the added active agent. The line or transition marked by 230 provides a further visual indicator of the demarcation between the two regions and their coloring.

Figures 3A, 3B:
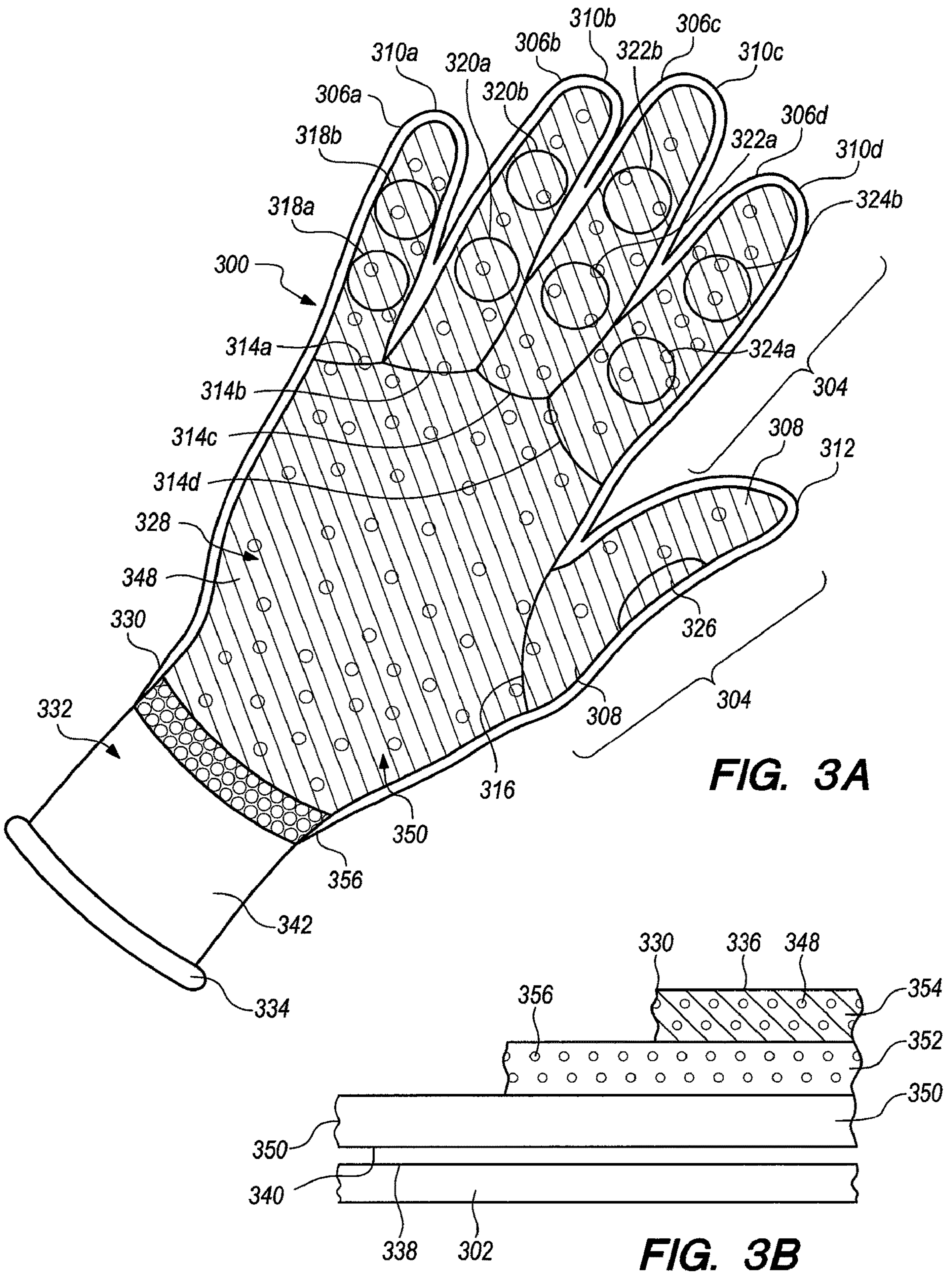
FIG. 3B is a cross sectional view taken from a portion of the glove in FIG. 3A illustrating a partial cutaway view of palm and cuff regions.

Referring now to FIGS. 3A-3B, wherein like components are numbered alike, another exemplary embodiment of a product membrane with a visual alert system and generally designated 300 is provided in the form of a glove for protecting a user's hand 302 is illustrated. As with the prior embodiments in FIGS. 1A-1B and FIGS. 2A-2B, the glove 300 contains includes a distalmost finger region 304 including four finger extensions 306*a-d* and a thumb extension 308 with each finger extending from a respective fingertip 310*a-d* and a thumb tip 312 and terminating at the base of each digit 314*a-d*, respectively, and the base of the thumb 316. The pinky finger extension 306*a* includes lower and upper knuckle regions, 318*a*, 318*b*, respectively. Similarly, the ring finger extension 306*b* includes lower and upper knuckle regions 320*a*, 320*b*, respectively. The middle finger extension 306*c* also includes lower and upper knuckle regions, 322*a*, 322*b*, respectively. The index finger extension 306*d* includes similar lower and upper knuckle regions 324*a*, 324*b*, respectively, as well. Finally, the thumb extension 308 includes a single knuckle region 326.

The glove 300 further includes a palm region 328 projecting from the base of each finger and thumb region 306*a-d* and 308 to a line of demarcation 330, which separates the palm region from a cuff region 332. At the innermost extent of the cuff region is a cuff or ring roll 334.

Referring now to FIG. 3B, the glove 300 is a multi-layer membrane with an outermost surface 336 and an innermost surface 340 for covering the wearer's skin 338 (FIG. 3B). Membrane product 300 contains at least three separate characteristics signified by separate colorations. Cuff region 332 includes a single layer membrane forming from an extension of the innermost layer 350 (FIG. 3B) that may or may not contain an active agent and features a first color indicated by unmarked region 344. Enlarged cuff line region 330 has a palm side transition and a spaced apart cuff side transition and is defined by an extension of an intermediate layer 352 (FIG. 3B) and appears above the cuff region 344 and below the palm region 328 that provides a built-in safety feature of an additional passive barrier layer of protection that may or may not contain an active agent 346 and may or may not be composed of two discrete layers, may be different elastomers and is separate from region 332 and features a second color indicated by the small circle pattern 356. Collective regions 304 (fingers) and 328 (palm) includes a two-layer membrane 354 defining the outermost surface 336 in that region with discrete separateness from region 332 and that may or may not contain an added active agent 346 and is indicated by a third color designated by the small circle pattern overlapped by diagonal lines 348. Furthermore discrete layers 354 that may compose region 304, 328 fuse together at region 330 to join to region 332 so that they are no longer discrete layers but a single membrane. Regions 304, 328 and 330 may denote a presence of location of properties and or components of the membrane product which are different from each other or different from each other and region 332 or have elements in common but are different none-the-less. The three different areas, 304/328, 330 and 332 may employ different colorations to visually exhibit and or communicate these different features to the viewer, and or user and or buyer. A property or component may include but is not limited to, a given number of membrane layers, which may range from one to more than one membrane layer, or a substance disposed in, on or incorporated into a membrane layer, such as a biocide, active agent, needle-treating materials, lubricant, spermicide, hydrogel or indicator or a combination of these. The variation in colors provides a visual indicator as to the presence, location, and/or specific type of built-in safety features available in the glove 300.

Figure 4:
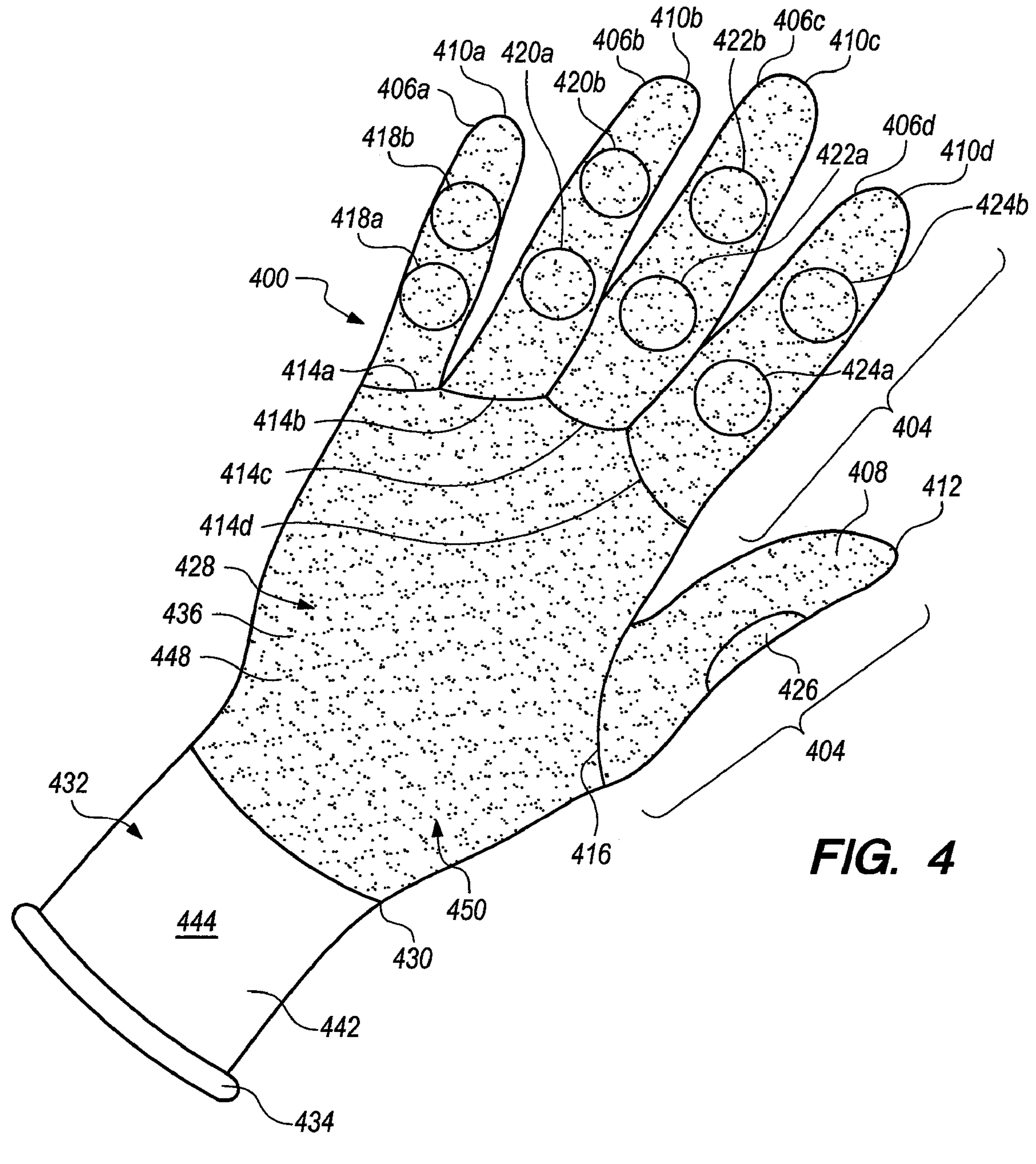

Referring now to FIG. 4, wherein like components are like numbered, another exemplary embodiment of a product membrane with a visual alert system and generally designated 400 is provided in the form of a glove for protecting a user's hand (not shown) is illustrated. As with the prior embodiments, this glove 400 contains includes a distalmost finger region 404 including four finger extensions 406*a-d* and a thumb extension 408 with each finger extending from a respective fingertip 410*a-d* and a thumb tip 412 and terminating at the base of each digit 414*a-d*, respectively, and the base of the thumb 416. The pinky finger extension 406*a* includes lower and upper knuckle regions, 418*a*, 418*b*, respectively. Similarly, the ring finger extension 406*b* includes lower and upper knuckle regions 420*a*, 420*b*, respectively. The middle finger extension 406*c* also includes lower and upper knuckle regions, 422*a*, 422*b*, respectively. The index finger extension 406*d* includes similar lower and upper knuckle regions 424*a*, 424*b*, respectively, as well. Finally, the thumb extension 408 includes a single knuckle region 426.

The glove 400 further includes a palm region 428 projecting from the base of each finger and thumb region 406*a-d* and 408 to a line of demarcation 430, which separates the palm region from a cuff region 432. At the innermost extent of the cuff region is a cuff or ring roll 434. As with the prior embodiments, the glove 400 may be used to cover a user's hand (not shown).

With continued reference to FIG. 4, the outermost surface 436 of the glove 400 exhibits a visual alert system as a first color tone within regions 404 and 428, collectively the protected region 450, as indicated by the shaded pattern 448, which is darker than the second color tone indicated by the unmarked area 444. In this exemplary embodiment, the darker tone is indicative of the presence of a built-in safety feature such as an active agent. The entire glove (product membrane) is constructed of one type of elastomer. It will be appreciated that any region in the glove may contain either no active agent (or other built-in safety feature) or a different active agent and an added dip of that agent. If an additional elastomer is dipped over a region, then this could result in a placement of the active agent between two elastomer layers resulting in a single-donning, triple laminate film in the manufacturing process. If the elastomer is translucent it may allow the color of a region to show through somewhat.

It will be appreciated that the glove product 400 may also be constructed with a multi-layer construction includes a first complete inner glove layer (cuff, palm and fingers) of inner elastomer incorporating an active agent of one composition and one color, a second layer film with an active agent and second color starting at the demarcation point 430 and extending through the palm and fingertip area and an additional complete outer layer (cuff, palm and fingers) of the same first material with the first active agent and the first color. When the glove product dries the three layers become a single layer article.

Figure 5:
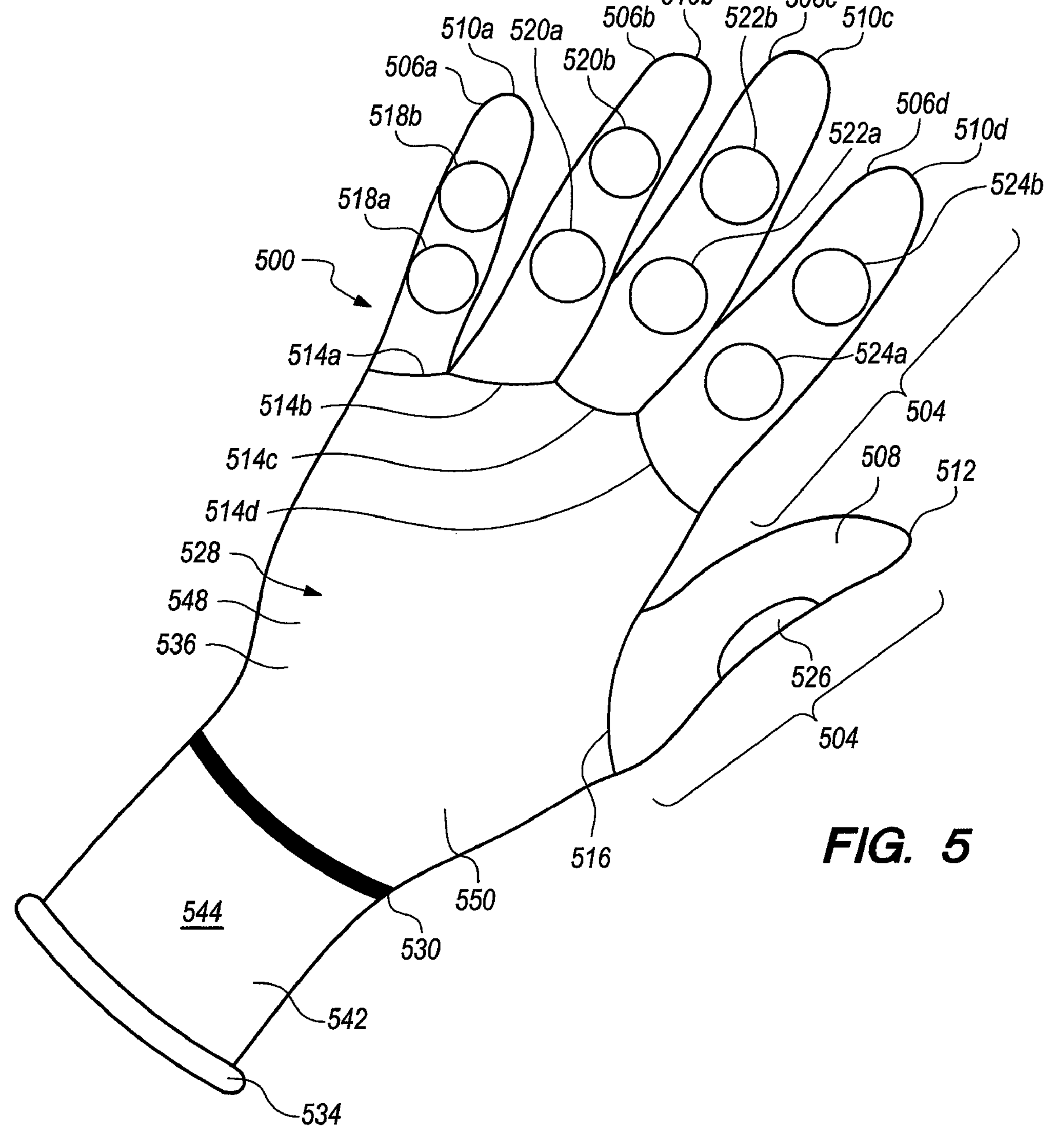

Referring now to FIG. 5, wherein like components are like numbered, another exemplary embodiment of a product membrane with a visual alert system and generally designated 500 is provided in the form of a glove for protecting a user's hand (not shown) is illustrated. As with the prior embodiments, this glove 500 contains includes a distalmost finger region 504 including four finger extensions 506*a-d* and a thumb extension 508 with each finger extending from a respective fingertip 510*a-d* and a thumb tip 512 and terminating at the base of each digit 514*a-d*, respectively, and the base of the thumb 516. The pinky finger extension 506*a* includes lower and upper knuckle regions, 518*a*, 518*b*, respectively. Similarly, the ring finger extension 506*b* includes lower and upper knuckle regions 520*a*, 520*b*, respectively. The middle finger extension 506*c* also includes lower and upper knuckle regions, 522*a*, 522*b*, respectively. The index finger extension 506*d* includes similar lower and upper knuckle regions 524*a*, 524*b*, respectively, as well. Finally, the thumb extension 408 includes a single knuckle region 526.

The glove 500 further includes a palm region 528 projecting from the base of each finger and thumb region 506*a-d* and 508 to a line of demarcation 530, which separates the palm region from a cuff region 532. At the innermost extent of the cuff region is a cuff or ring roll 534.

With continued reference to FIG. 5, the glove 500 is a single layer membrane with an outermost surface 536 and an innermost surface (not shown) for covering the wearer's skin 538 (not shown). The outermost surface includes a line of demarcation 530, that has been printed or otherwise deposited onto the membrane signifying the color change from region 550 (encompassing both finger region 504 and palm region 528) featuring a first color and adjacent cuff region 532 featuring another color and each of these colors communicating different characteristics of the glove such that region 550 may or may not contain an active agent and region 532 is devoid of that active agent. Exemplary demarcations 530 may be, but are not limited to, thin, thick, or shaded lines, curves, dashes, or shapes, or any other design visible to a user of membrane product 500. Demarcation 530 could, but need not, mark a boundary between a presence and absence of a component or components. For examples, an active agent could be present in region 532 but not in region 550. In this embodiment, region 550 contains an active agent and demarcation 530 denotes where the active agent ends. Alternately or additionally, the coloring configuration could be used to denote the presence of properties, layers and or components in region 550 as being distinct and different from those in region 532.

Figure 6:
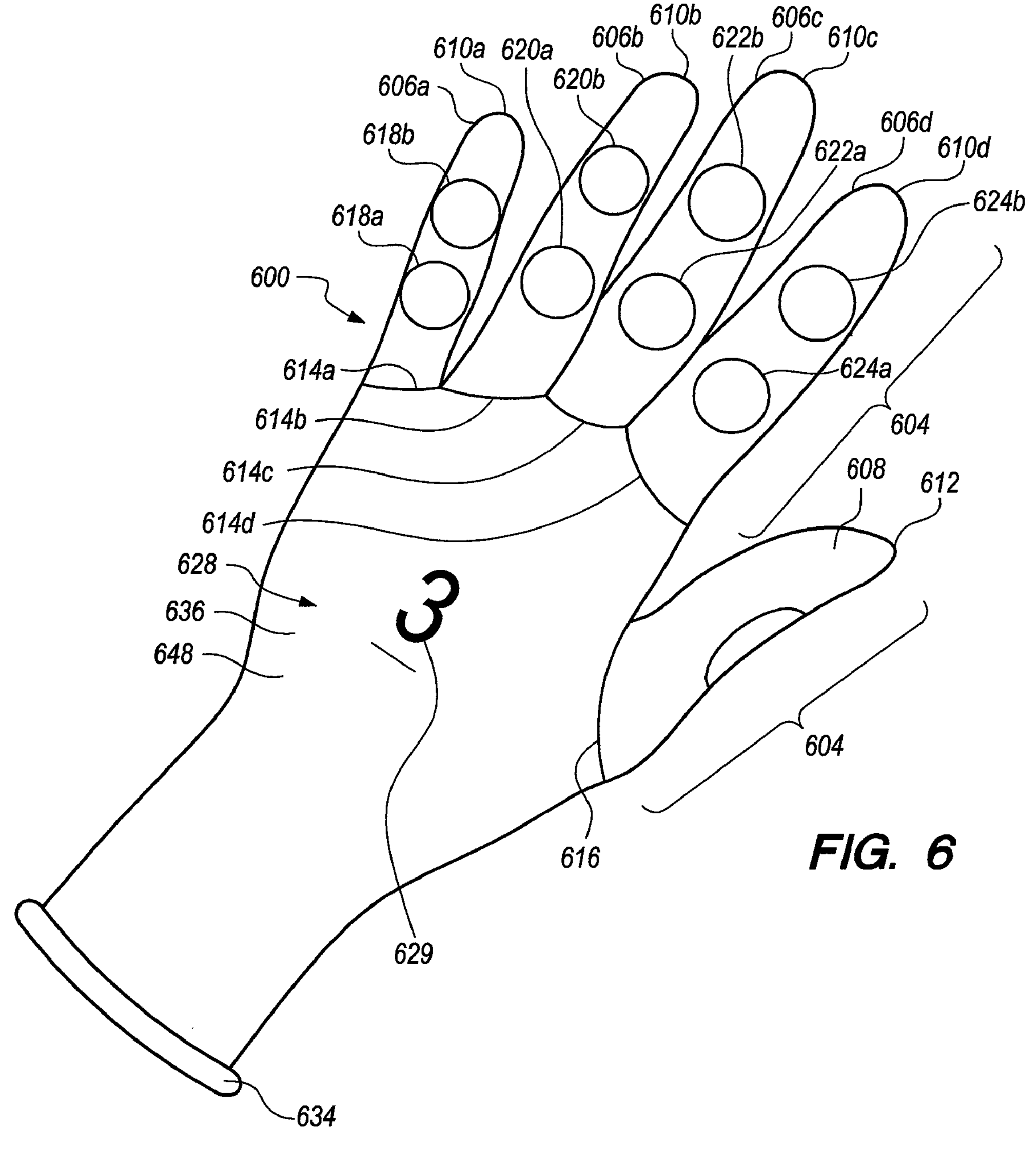

Referring now to FIG. 6, wherein like components are like numbered, another exemplary embodiment of a product membrane with a visual alert system and generally designated 600 is provided in the form of a glove for protecting a user's hand (not shown) is illustrated. As with the prior embodiments, this glove 600 contains includes a distalmost finger region 604 including four finger extensions 606*a-d* and a thumb extension 608 with each finger extending from a respective fingertip 610*a-d* and a thumb tip 612 and terminating at the base of each digit 614*a-d*, respectively, and the base of the thumb 616. The pinky finger extension 606*a* includes lower and upper knuckle regions, 618*a*, 618*b*, respectively. Similarly, the ring finger extension 606*b* includes lower and upper knuckle regions 620*a*, 620*b*, respectively. The middle finger extension 606*c* also includes lower and upper knuckle regions, 622*a*, 622*b*, respectively. The index finger extension 606*d* includes similar lower and upper knuckle regions 624*a*, 624*b*, respectively, as well. Finally, the thumb extension 408 includes a single knuckle region 626.

The glove 600 further includes a palm region 628 projecting from the base of each finger and thumb region 606*a-d* and 608 to a line of demarcation 630, which separates the palm region from a cuff region 632. At the innermost extent of the cuff region is a cuff or ring roll 634.

With continued reference to FIG. 6, the glove 600 is a single layer membrane with an outermost surface 636 and an innermost surface (not shown) for covering the wearer's skin 638 (not shown). The outermost surface 636 exhibits a symbol which may or may not be a number imprinted on the body of the glove signifying a certain characteristic or characteristics of the glove which may be the number of layers, the number of active agents and or other characteristics. The imprint may be, but is not limited to, one or more lines, curves, shapes, logos, patterns, or designs that are colored, black or translucent. The imprint may be printed on the inside or outside of one or more layers of the membrane product 600. Different imprints on a single glove may be used to denote specific properties or components included in particular membrane product. For instance if the membrane product is configured partially of two discrete layers an imprint signifying this feature could be printed on what becomes an inner layer and be seen through a translucent outer layer to distinguish itself as a visual indication to a user that membrane product 600 is a multi-layer membrane product. An imprint may occur during or after the manufacturing process but before the packaging and sterilization process. An imprint may also be composed of a message to the user or describe in words a feature(s) of the product. In this exemplary embodiment 600, the visual indicator or imprint is the number "3" (designated by reference numeral 629) in region 628 that indicates this glove contains three layers of protection.

Figure 7:
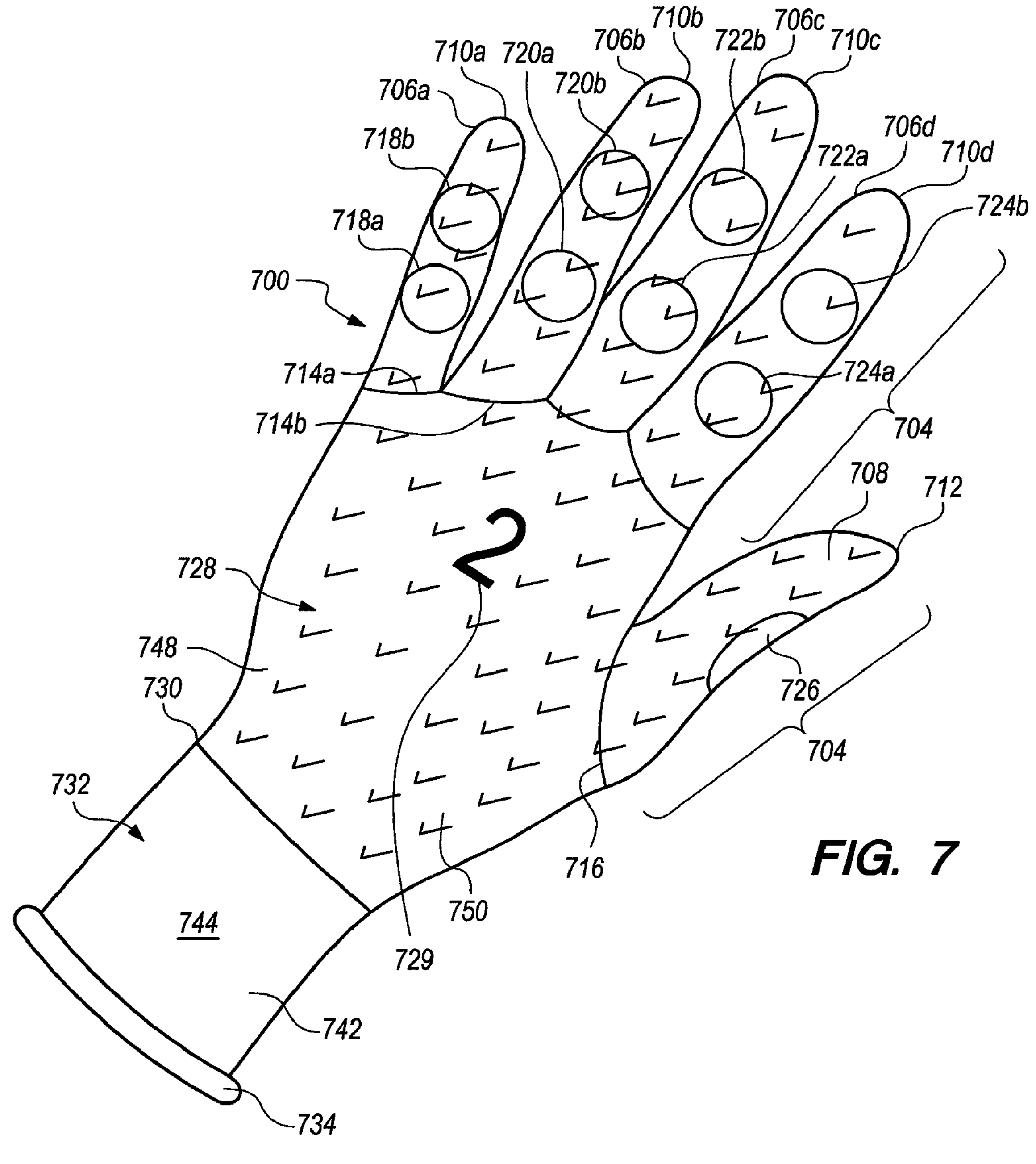

Referring now to FIG. 7, wherein like components are like numbered, another exemplary embodiment of a product membrane with a visual alert system and generally designated 700 is provided in the form of a glove for protecting a user's hand (not shown) is illustrated. As with the prior embodiments, this glove 700 contains includes a distalmost finger region 704 including four finger extensions 706*a-d* and a thumb extension 408 with each finger extending from a respective fingertip 710*a-d* and a thumb tip 712 and terminating at the base of each digit 714*a-d*, respectively, and the base of the thumb 716. The pinky finger extension 706*a* includes lower and upper knuckle regions, 718*a*, 718*b*, respectively. Similarly, the ring finger extension 706*b* includes lower and upper knuckle regions 720*a*, 720*b*, respectively. The middle finger extension 706*c* also includes lower and upper knuckle regions, 722*a*, 722*b*, respectively. The index finger extension 406*d* includes similar lower and upper knuckle regions 724*a*, 724*b*, respectively, as well. Finally, the thumb extension 408 includes a single knuckle region 726.

The glove 700 further includes a palm region 728 projecting from the base of each finger and thumb region 706*a-d* and 708 to a line of demarcation 730, which separates the palm region 728 from a cuff region 732. At the innermost extent of the cuff region is a cuff or ring roll 734. The glove 700 is a single layer membrane with an outermost surface 736 and an innermost surface (not shown) for covering the wearer's skin (not shown). Here, the palm region 728 and finger region 704 collectively form the discrete layers region 750.

In this exemplary embodiment, the product membrane 700 includes the symbol for the number "2", denoted by the number 729, on the palm area of region 750. Region 750 is of one color as indicated by the check mark pattern 748 and that may or may not indicate the palm area is composed of additional discrete or non-discrete layers of elastomer and or one or more additional active agents that may or may not be in the inner portion of the palm area of region 750 and or may or may not indicate features related to different construction than that featured in the cuff area of another color, indicated by unmarked area 744 in region 732. This symbol can be imprinted on what becomes the outer layer and covered by another membrane layer that becomes translucent so that the imprint shows itself to the user. Thus, the visual indicator in this exemplary embodiment is both a symbol and a set of contrasting colors to indicate both the presence and location of the built-in safety features, either passive or active, of the glove 700.

Figures 8A, 8B:
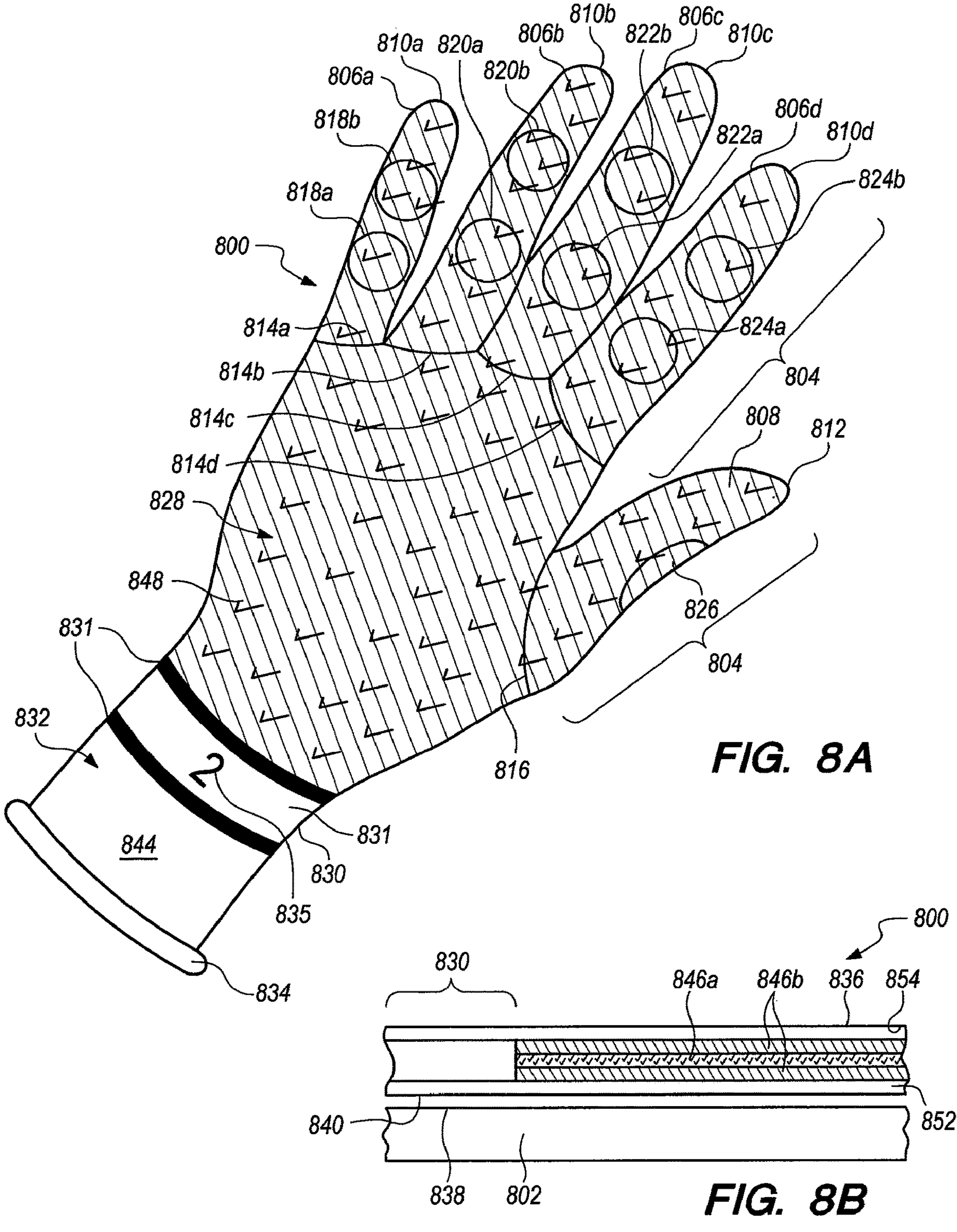
FIG. 8B is a cross sectional view taken from FIG. 8A illustrating a partial cutaway view of palm and cuff regions.

Referring now to FIGS. 8A-8B, wherein like components are like numbered, another exemplary embodiment of a product membrane with a visual alert system and generally designated 800 is provided in the form of a glove for protecting a user's hand 802 is illustrated. As with the prior embodiments, this glove 800 contains includes a distalmost finger region 804 including four finger extensions 806*a-d* and a thumb extension 408 with each finger extending from a respective fingertip 810*a-d* and a thumb tip 812 and terminating at the base of each digit 814*a-d*, respectively, and the base of the thumb 816. The pinky finger extension 806*a* includes lower and upper knuckle regions, 818*a*, 818*b*, respectively. Similarly, the ring finger extension 806*b* includes lower and upper knuckle regions 820*a*, 820*b*, respectively. The middle finger extension 806*c* also includes lower and upper knuckle regions, 822*a*, 822*b*, respectively. The index finger extension 806*d* includes similar lower and upper knuckle regions 824*a*, 824*b*, respectively, as well. Finally, the thumb extension 808 includes a single knuckle region 826.

The glove 800 further includes a palm region 828 projecting from the base of each finger and thumb region 806*a-d* and 808 to a line of demarcation 830, which separates the palm region from a cuff region 832. At the innermost extent of the cuff region is a cuff or ring roll 834.

Referring now to FIG. 8B, the glove 800 is a multi-layer membrane with an outermost surface 836 and an innermost surface 840 for covering the wearer's skin 838. In addition, a first active agent 846*a* (intermediary checkmarked region) or substance disposed between the membrane between the outermost layer 854 and innermost layer 852 and also between a second active agent 846*b* (vertical line regions) or substance. Such construction may provide a reservoir encased by other layers of the glove where the active agents or other substances are stored.

In addition, the glove 800 is marked proximate the cuff region 830 of one color 831 between two lines 833 or stripes on either side of the number "2", indicated by reference numeral 835 which may or may not be of a different color than region 832. A symbol such as the number "2" may be used to indicate the presence of one or more discrete layers beginning and ending in the region or one or more non-discrete layers beginning at the top of the region and that also or may or may not contain an alternative element or additional elements. Above region 830 is the non-cuff area, region 850, including the palm region 828 and finger region 804 with a different color that may or may not feature the presence of one or more discrete layers and or the presence of one or more non-discrete layers and or a reservoir space which may or may not contain a substance 846*a*, 846*b* in said reservoir. The substance 846*b* may be an active agent that is also a dye or is colored by a colorant. The substance 846*b* may be deposited such that it may be carried by a sharp object passing through it resulting in a visible transfer of the colored substance to an article of clothing of the wearer and or the skin of the wearer in such manner as to imprint or tattoo it with the color of the substance.

Figure 9:
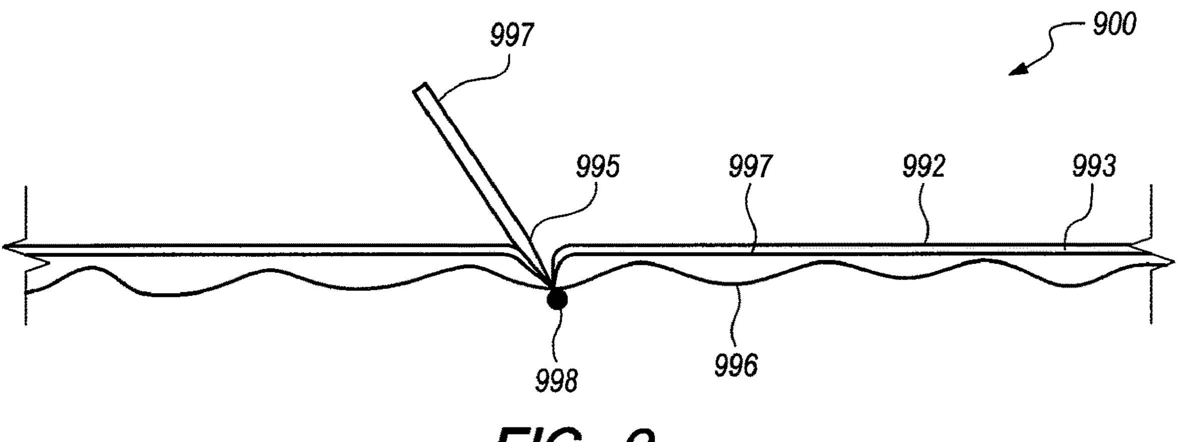
FIG. 9 is a cross sectional view of a portion of an exemplary membrane product such as that in FIG. 1 constructed in accordance with the principles of the present invention and depicting the placement of a puncture marking.

Referring now to FIG. 9, representing a portion of a membrane product such as those membrane products disclosed above, a colorant or dye 993 is disposed between the innermost surface 994 and outermost surface 992, of the membrane product. Should a sharp object 997 depress a portion of the membrane as shown at region 995 and penetrate the innermost layer 994 to either contact or penetrate the skin 996 of the wearer, the colorant or dye will be carried by the sharp 997 and create a puncture marker 998, also referred to as a tattoo, on or in the skin of the wearer. In this manner, the user's skin may be marked with a visual indicator where a sharp contact is made, either onto, into, or below the epidermal layer of the skin. This may be done repeatedly for multiple contacts as well.

It will be appreciated that the puncture marker is preferably difficult to remove such that removal of the membrane product or sliding of membrane product against the user's skin will not remove or smear the mark. The colorant or dye may be in the form of a pigment alone or carried in a carrier solution as would be understood by one of ordinary skill in the tattooing arts. The pigment provides the color of the tattoo. The purpose of the carrier is to disinfect the pigment suspension, keep it evenly mixed, and provide for ease of application. Some exemplary pigments may be made from a mixture of one or more of the following materials (per color) that include, but are not limited to, black made from a compound of Iron Oxide ($Fe_3O_4$), Iron Oxide (FeO), Carbon, and Logwood; brown made from ochre; red made from Cinnabar (HgS), Cadmium Red (CdSe), Iron Oxide ($Fe_2O_3$), and Napthol-AS pigment; orange made from disazodiarylide and/or disazopyrazolone, cadmium seleno-sulfide; flesh colors made from Ochres (iron oxides mixed with clay); yellow made from Cadmium Yellow (CdS, CdZnS), Ochres, Curcuma Yellow, Chrome Yellow ($PbCrO_4$, often mixed with PbS), disazodiarylide; green made from Chromium Oxide ($Cr_2O_3$), called Casalis Green or Anadomis Green, Malachite [$Cu_2(CO_3)(OH)_2$], Ferrocyanides and Ferricyanides, Lead chromate, Monoazo pigment, Cu/Al phthalocyanine, Cu phthalocyanine; blue from Azure Blue, Cobalt Blue, Cu-phthalocyanine; violet made from Manganese Violet (manganese ammonium pyrophosphate), Various aluminum salts, Quinacridone, Dioxazine/carbazole; and white made from Lead White (Lead Carbonate), Titanium dioxide ($TiO_2$), Barium Sulfate ($BaSO_4$), and Zinc Oxide.

It is preferred that the dye stick or otherwise adhere to the sharp to increase the accuracy of the placement of the puncture marker relative to the sharp puncture into the user's skin. An oily, sticky, or gummy substance may be used in the carrier solution or on the pigment to increase adherence to a sharp passing through. Another potential substance to use is gentian violet in a powdered, crystal, granular, or flake form. Alternatively, the biocide or anti-microbial substance may also be treated to form a solution with a powdered, crystal, flake, or granular component. Either alternative incorporating a non-liquid ("dry") component will improve the likelihood of the sharp forcing some of the dry components into the user's skin similar to an inoculation or implant process instead of simply allowing a liquid dye to seep or leak out like a stain as in the Fuchs patent discussed in the background section. In either case, the dry ingredients may form a pin point mark where the sharp encounters the user's skin or may bloom into a larger marking or into a specific color either upon contact with the moisture in the skin or when exposed to air once the gloves are removed. The dry ingredients may be immersed or encapsulated in a liquid as well. The distinct visual alert created by the puncture marker will improve the likelihood of detecting a sharp puncture, particularly, after the gloves are removed.

As noted earlier, a membrane product 100-900 may include one or more properties or components that may be identified by coloration or other markings according to the present invention. For example, an intermediate layer or layers of a multi-layer membrane may include a needle-treating or sharp object-treating layer or layers. A membrane product may be of natural latex and or synthetic layer or polymer. A membrane may include an indicating substance. Multi-color membranes products according to the present invention, in addition to or instead of indicators, may also include one or more reservoirs disposed between adjacent membrane layers and containing one or more component substances. A property of a membrane product may include its number of membrane layers, discrete membrane layers such as the discrete double-layer property of the glove illustrated in FIG. 7. A space between discrete membrane layers may serve as a reservoir to contain a variety of component substances as well and component substances may be introduced on, and/or into polymer during or subsequent to fabrication of the membrane or membrane layers. A membrane product may also include membrane reinforcement materials.

With reference to FIGS. 1A-8, it may be appreciated that packaging for these products may reflect the visual representations of the certain product colorations and markings. This close relationship between the product visual design and the container and or packaging reflecting this design will further serve to expedite the selection of the product, one from another, especially in a harried environment. The user can visually choose a product quickly because the containers and or package design reflects the appropriately colored and or marked design of the product which in turn reflects the product benefits and levels of protection appropriate to the job at hand and communicated visually by this invention.

As used herein, the term protected or protection is used herein to define a region of the membrane product that has at least one built-in safety feature, whether passive or active. Each built-in safety feature is defined by a set of attributes or properties including, but not limited to, a presence, a general or specific location, and a prevention type. FIG. 13 displays a matrix, generally designated 1300, with a set of built-in safety features that may be incorporated into the membrane products constructed in accordance with the principles of the present invention. In the upper portion 1302 of the matrix, a set of general trait identifiers is listed in the first column next to their corresponding traits, characteristics, components, or properties. These general traits are typically binary in nature, that is, there are two states (second and third columns next to each general trait identifier in the first column) associated with each general trait. For example, an active feature (general trait—first column) is either not present (first state—second column) or present (second state—third column). Similarly, an active feature (general trait) has a general location (first state) or a specific location (second state) while a region (general trait) may generally be devoid of any feature (first state) or have a specific area devoid of any feature (second state). The active agent may be disposed in a reservoir between layers or surfaces or disposed within a layer (e.g., impregnated within the matrix of a layer). The lower portion 1304 of the matrix 1300 includes an exemplary set of specific traits identifiers in the first column in line with their corresponding trait details in the second, third, and fourth columns. Here, the trait details may be endless. In this exemplary matrix, each specific trait has three states. For example, the active agent type (specific trait identifier—first column) made be selected from: biocide (first trait option—second column), antimicrobial (second trait option—third column), or gentian violet (third trait option—fourth column) or the number of layers (specific trait identifier) may be single (first trait option), multi-layer fused (second trait option), or multi-layer discrete (third trait option). In general, these exemplary safety traits are found throughout this application and summarized in FIG. 13.

Turning now to FIG. 14, a visual indicator matrix 1400 is illustrated. The visual indicator matrix includes a set of exemplary visual indicators that may be used with a membrane product to indicate one or more of the safety traits in the trait matrix 1300 in the FIG. 13 are built-in to that membrane product. It will be appreciated that, by mixing and matching the visual alert indicators with one or more corresponding traits, a visual alert system and applying or incorporating such visual indicators to the membrane products in a prominent, visually perceptible position, information regarding built-in safety features including the presence, location, and specific type of safety features may be rapidly conveyed to the wearer or person selecting the membrane products. There is no restriction as to which visual indicator may be used with a particular safety feature or group of safety features.

Methods of Manufacturing the Membrane Products:

Referring now to FIGS. 10-12C, further description now follows of single and multi-layer membranes which include one or more of these properties and or components (built-in safety features with visual indicators) and of methods for making the membranes that feature one or more colors, non-colors or different tone marking these differences, features and or imprints according to the present invention. In describing the processes below, it will be understood that the processes are broken down into a series of steps or stages and that an interim product will be produced after each step, starting with the creation of a base layer and progressing through the steps until the final resultant product.

The glove dipping process can be completed using various types of manufacturing equipment designs. The terms 'former' and 'mold' may be used interchangeably but both mean the form on which the glove article is made which is in the shape of the glove product. The two more familiar manufacturing designs are continuous line dipping which can be single glove formers, multiple formers per attachment. The second is batch dipping in which several formers are attached to a board and are then moved through the dipping process via individual stations positioned underneath them. The glove according to the present invention may be manufactured using any variation of these manufacturing processes and or additionally suitable manufacturing processes. The compound used to form the glove product can be made either out of a latex or a polymer or an elastomer compound or a mix of layers of each. For the manufacturing example below, latex will be used but it is appreciated that the products may be made from a polymer as well as other elastomers. That said the process may be altered to allow a different layer(s) of either compound in the making of one article.

Figure 10:
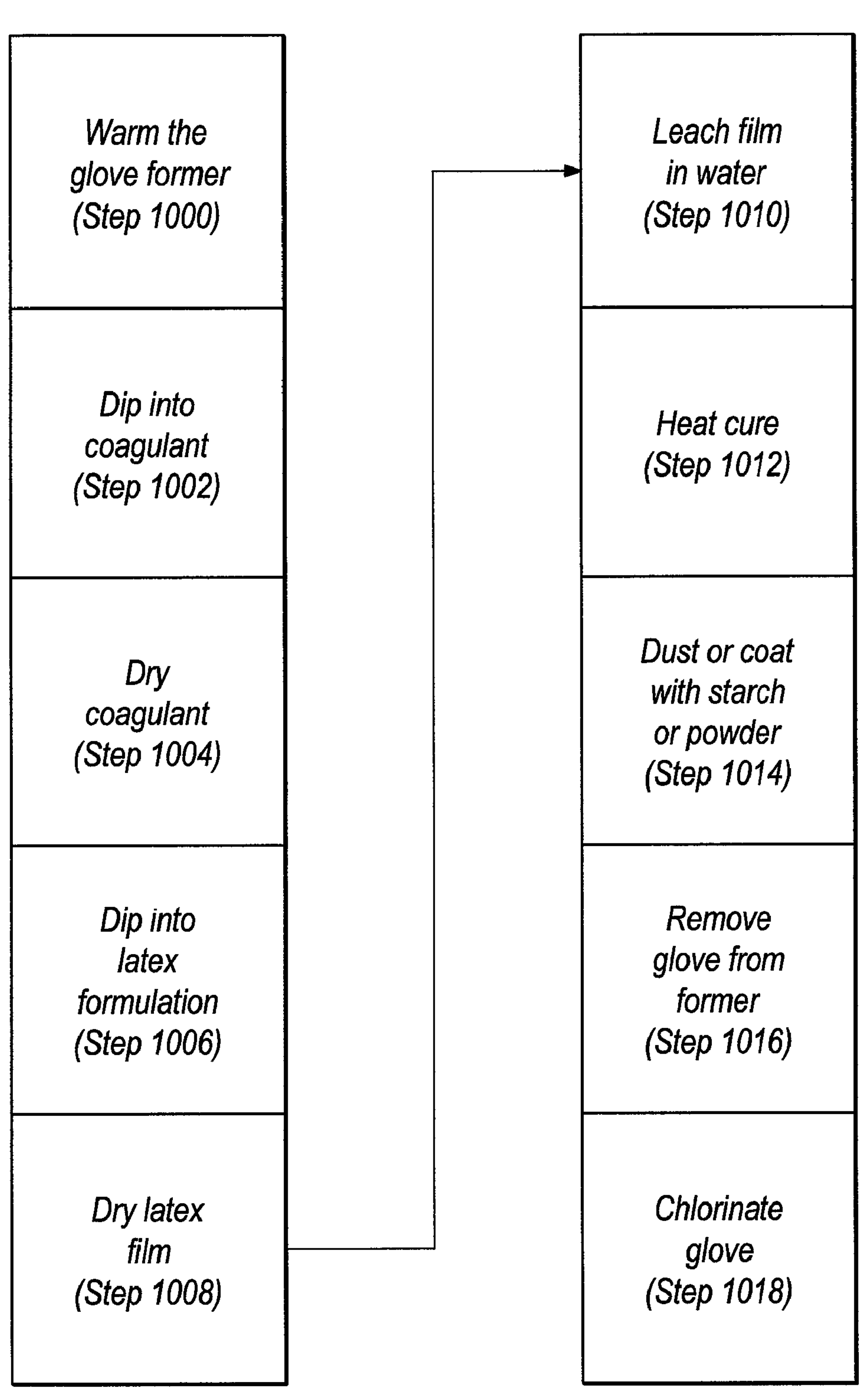
FIG. 10 is a process diagram illustrating a process for manufacturing a conventional latex glove.

Referring now to FIG. 10, a standard, conventional glove dipping process is illustrated. At step 1000, the process is initiated by warming the glove former. At step 1002, the glove former is dipped in a coagulant. At step 1004, the coagulant is allowed to dry. At step 1006, the dried coagulant is dipped into a latex formulation. The latex film is allowed to dry at step 1008. The latex film is then leached in water at step 1010. The leached latex film is heat cured at step 1012. At step 1014, the heat cured product is dusted or coated with starch or powder. At step 1016 the glove is removed from the former. The glove is then chlorinated if desired at step 1018.

Figure 11A:
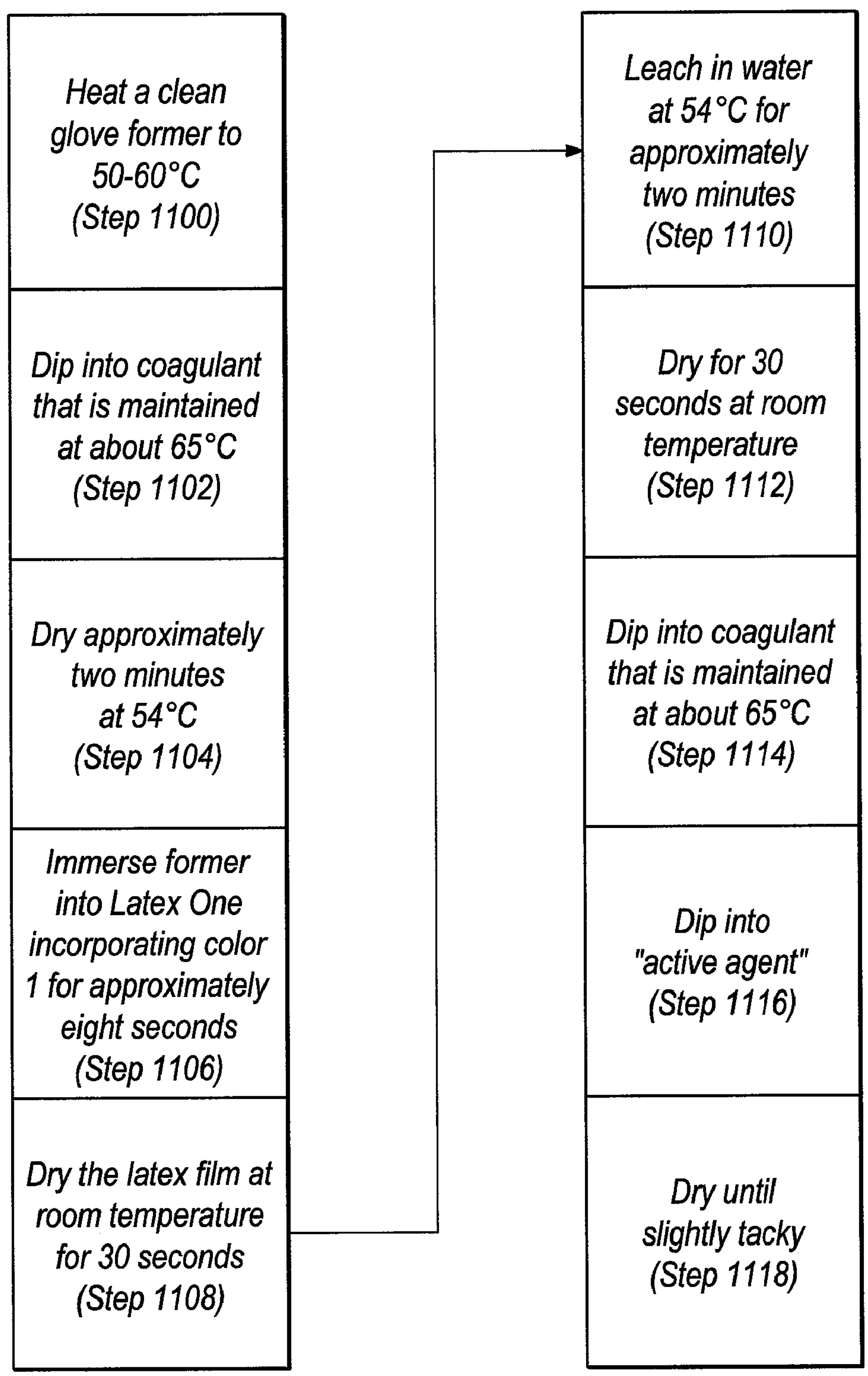
Figure 11B:
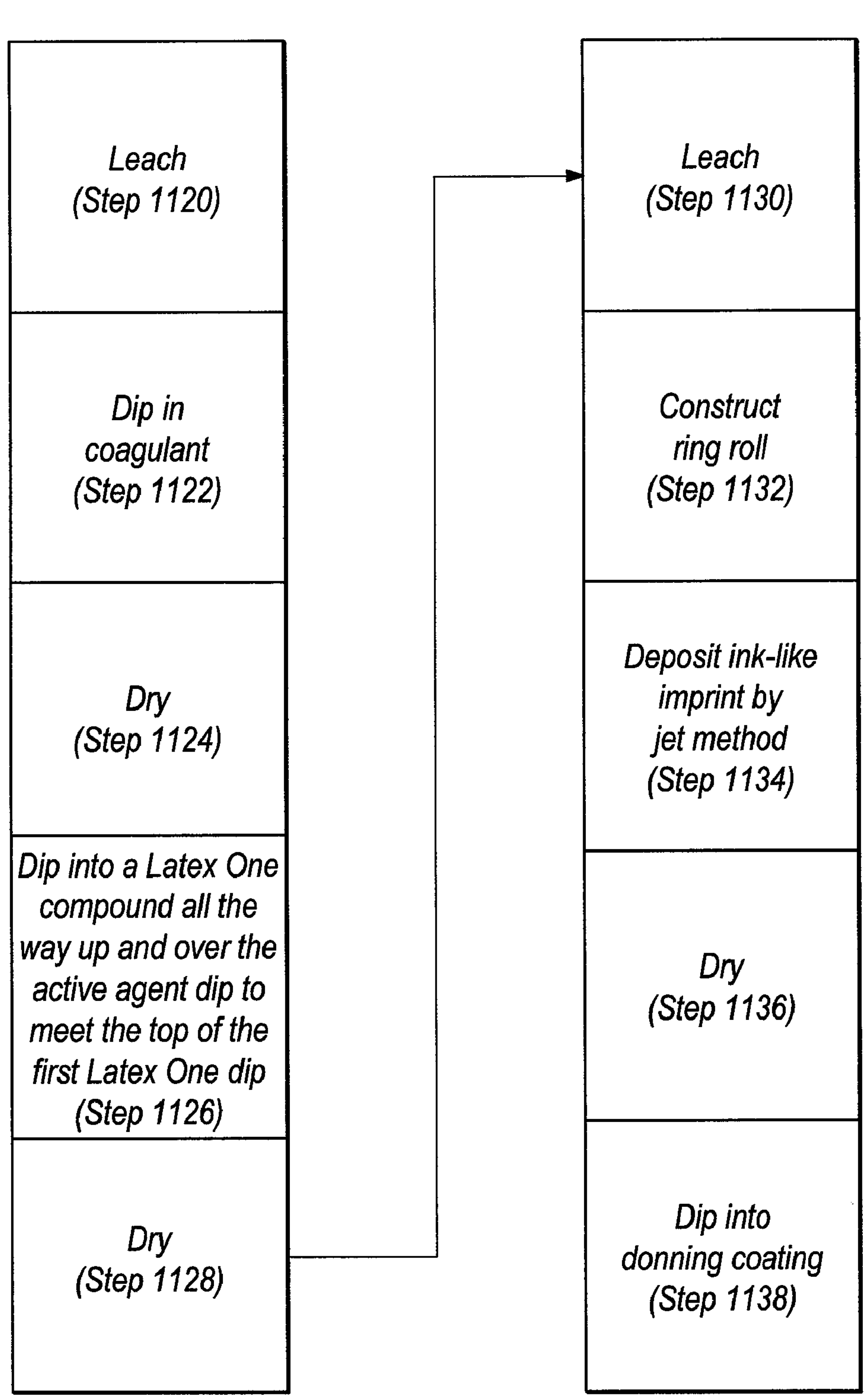

Method of Making Multi-Colored Active and Non-Active Membrane Products, Including Imprint Features, and Dye Transfer Tattooing Features:

Referring now to FIGS. 11A-C, an exemplary process for making multi-colored active or non-active membranes including imprint features, and/or dye transfer tattooing features is illustrated. Starting with step 1100 in FIG. 11A, after the glove former is cleaned, the glove former is then heated to a range of 50-60 degrees Celsius. The former is dipped into a coagulant that is maintained a temperature of about 65 degrees Celsius at step 1102. The glove formers are dipped into a coagulant bath to help the latex mixture adhere to the formers and help ensure the latex is distributed evenly. The coagulant tank stage determines the thickness of the latex exam glove. The thicker the requirements for the disposable gloves are, the longer the formers will travel in the coagulant tank. At step 1104, the coagulant is dried approximately two minutes at 54 degrees Celsius. At step 1106, the former is immersed into Latex One (latex formulation) incorporating color 1 (the first color) for approximately eight seconds. The compound may be of a formulation to be translucent at end of process enough to allow the "active agent" region on the finished product to show through as a different color than the non-active region of the finished product. The latex mixture will have different formulations depending on the type of gloves being made. Continuing with FIG. 11A, at step 1108, the latex film travels through a series of ovens or other drying equipment and is dried at room temperature for 30 seconds. At step 1110, the latex film is leached in water at 54 degrees Celsius for approximately two minutes. The gloves are put through a leaching line to remove residual chemicals and proteins from the surface of the gloves. At step 1112, the leached interim product is dried for thirty seconds at room temperature. At step 1114, the dried product is then dipped into a coagulant that is maintained at about sixty-five degrees Celsius. At step 1116, the interim product is then dipped into an "active agent", which is also a purple dye, and may be composed of; by weight, 1% crystal violet, 3% wax #09730 and 96% deionized water, over the present layer of Latex One but stopping approximately 3 inches short of the top of wrist portion of the former. This "active agent" area needs a strong enough dye, color, to show through the latex formulation (on the finished product) that is dipped on top of it in step 14. The interim product is then dried until slightly tacky at step 1118.

Continuing on with FIG. 11B, at step 1120, the product is leached. At step 1122, the product is dipped into a coagulant a second time. At step 1124, the product is dried. At step 1126, the dried interim product is then dipped into a Latex One compound all the way up and over the active agent dip to meet the top of the first Latex One dip. At step 1128, the interim product is dried. At step 1130, the interim product is leached. At step 1132, the ring roll in constructed. At step 1134, an ink-like imprint is deposited using an ink-jet method. At step 1136, the interim product is then dried again. At step 1138, the dried product is dipping into a donning coating.

Continuing on with FIG. 11C, at step 1140, the interim product is dried. At step 1142, the membrane product is removed from the former. The membrane product is then chlorinated, if desired, at step 1144, to make the gloves less tacky. At step 1146, the chlorinated product is dried. The resultant product is achieved at step 1148. The gloves may be tested for leaks using air pressure and water pressure testing procedures as well.

Alternatives to chlorination for making the gloves less tacky includes applying a powder, such a cornstarch, or a hydrogel coating toward the end of the process.

This process results in a finished glove product (step 1148) which is two-colors or bi-color—one color at the top of wrist area, (cuff), that extends for about 3 inches to a point that the color changes to a different color to visually show the presence of the "active agent" until it reaches the end of the glove at the fingertips. One can now distinguish a glove with an 'active agent' to a glove without an "active agent". The color demarcation shows exactly where the 'active agent' is positioned—where it begins and ends. The color indicates the presence and benefit of an increased layer of active protection in that area of the product—where injuries occur. Different colors may also indicate the protection benefits of certain compounds. For example a glove with an orange antimicrobial section may always indicate an added barrier to viruses while a turquoise antimicrobial section may always indicate the glove features extra protection against bacteria. And additionally, features and benefits may be communicated with imprinted wording such as "Anti-Bacterial".

The dwell time in the "active agent" solution and the concentration of the "active agent" utilized affect the concentration of "active agent" absorbed by the latex film. A typical dwell time in the "active agent" solution is 30 seconds at room temperature. The "active agent"-coated latex film is then dried for two minutes at 54° C. to promote adhesion to the latex film. Correct drying promotes adhesion of the antimicrobial to the latex film and improves the homogeneity of the coating. While the "active agent" substance may be selected from a wide variety of known materials, a preferred "active agent" substance includes a mixture on an approximate percentage basis by weight of 1% crystal violet, 3% wax #09730 and 96% deionized water.

The second latex dwell, preferably about 15 seconds, is used to produce the desired thickness of the final glove. The entire latex article is then dried for two minutes at 54° C. to prepare it for the donning coating application. The glove may be leached again at this time and the ring roll configured at this point in the process. After the drying process all the layers will bond together to form a single glove article that is essentially a tri-laminate but of two colors. Conversely if some of the layers act as separating agents during the process which can be caused by variations in the coagulant and or where it is placed and or the antimicrobial, some layers may 'pop apart' or separate in the process of drying to make a glove product featuring discretely separated films or layers but still attached to the cuff area which did not contain any separating compounds between layers.

It will be appreciated that the active agent may be deposited on the elastomer dip during the manufacturing process and or incorporated into the glove as a partial coagulant partially bonding to the first latex dip or dipped on top of the coagulant and allowing pick-up of the second latex dip. The active agent may also be dipped on top of or under any of the elastomer films as they are dipped and or processed. In dipping the active agent it may be dipped onto the former up to any specified point. This could be as much as three inches from the top of the cuff line of the glove so that one can see a white or first color latex film cuff and further down see the "active agent" dip which is a different color or different tone of the latex first color. At this point one can see the line of demarcation between the two layers and two colors, one above the other, The first color compound is visible above the second color compound. Another way to look at it is that this second latex dip goes over the antimicrobial dip and extends up to the exact place where the fist latex dip ends so that the cuff area of the article being dipped is of one color (two dips of latex fused together in the oven upon curing) and the body of the article being dipped is of a second color with a clear demarcation between the two colors. The body color contains the antimicrobial element and the cuff area does not. It may be appreciated that both latex dips may include antimicrobial elements in their formulation. In another variation, the process results in both the cuff and body area of the glove being made of different antimicrobial compounds and exhibiting different antimicrobial properties.

It is also appreciated that the application of the "active agent" may precede step 1106 and or follow steps, 1136, 1138 or 1144.

The application of a donning coating is completed by immersing the latex film and withdrawing the film from the donning solution at a controlled speed. The donning coating is dried for 30 seconds at room temperature and then the former proceeds to the cure oven.

The glove is cured for 20 minutes at 130° C., allowed to cool and is then stripped from the former and inverted, (or 'straight-dipped' off) chlorinated and dried.

Any of the latex or polymer layers may contain a colorant, dye or active component.

Steps of this dipping and leaching process may be repeated for as many times as desired to build up thicknesses that can include additional coagulant and drying and leaching and curing steps.

The "active agent", may be defined as a biocide or antimicrobial. The desired agent for this embodiment is gentian violet as it can have both dye and antimicrobial properties. The 'active agent', such as an antimicrobial or biocide may be colored and or contain a dye. It is deposited on the elastomer dip during the manufacturing process and or incorporated into the glove as a partial coagulant partially bonding to the first latex dip or dipped on top of the coagulant and allowing pick-up of the second latex dip. It may also be dipped on top of or under any of the elastomer films as they are dipped and or processed. It may also be dissolved in the elastomer(s) and or coagulant mixture.

It is appreciated that the process for making multi-colored membranes including imprint(s) feature can, with variations on the same invention process, produce a multi-colored membrane with a single wrist portion and one of more discrete layers with or without "active agent" in, on or between discrete and non-discrete layers. Some ways in which the initial process can be varied to produce glove products with visual puncture indicators or added protection are described below. It should be appreciated that more variations are able to be instructed by changing any combinations of the elements and steps so stated in the process.

It is appreciated that an "active agent" may be added to the latex compound also and a different color or imprint symbol can signify this as, for example, membrane product 100, FIG. 1 and membrane product 500, FIG. 5.

This glove may or may not have an imprint. If the glove is to be inverted when it is stripped, the imprint step should take place after 1108 above and positioned so that when glove is inverted the symbols reads or shows itself properly as, for example, membrane product 500, FIG. 5.

The "active agent" latex film can be leached at this point and or is immersed and removed from a powder-free or standard coagulant and dried for two minutes at 54° C. prior to entering a second compounded latex dip of the same color as the first latex dip.

Figure 12A:
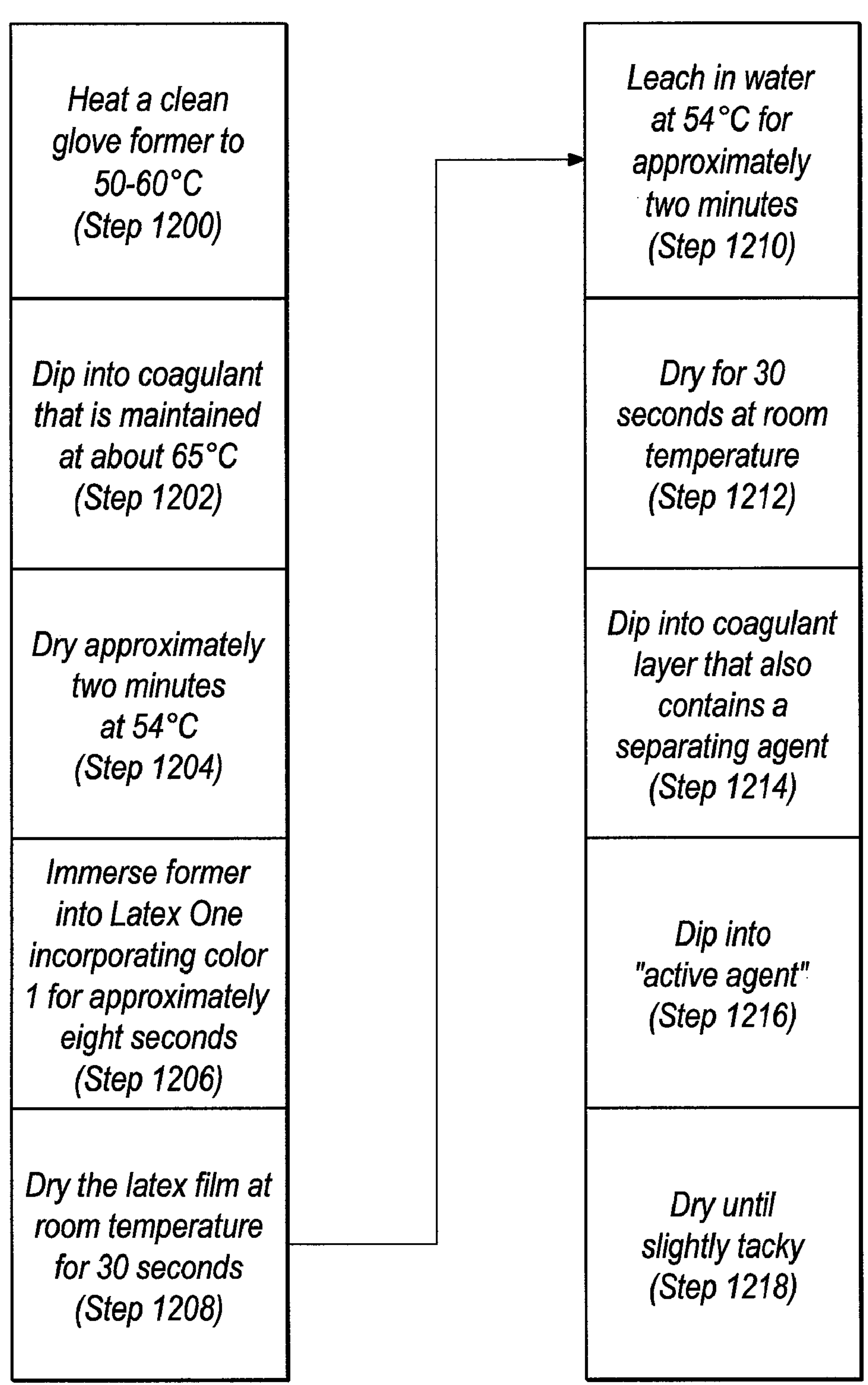
Figure 12B:
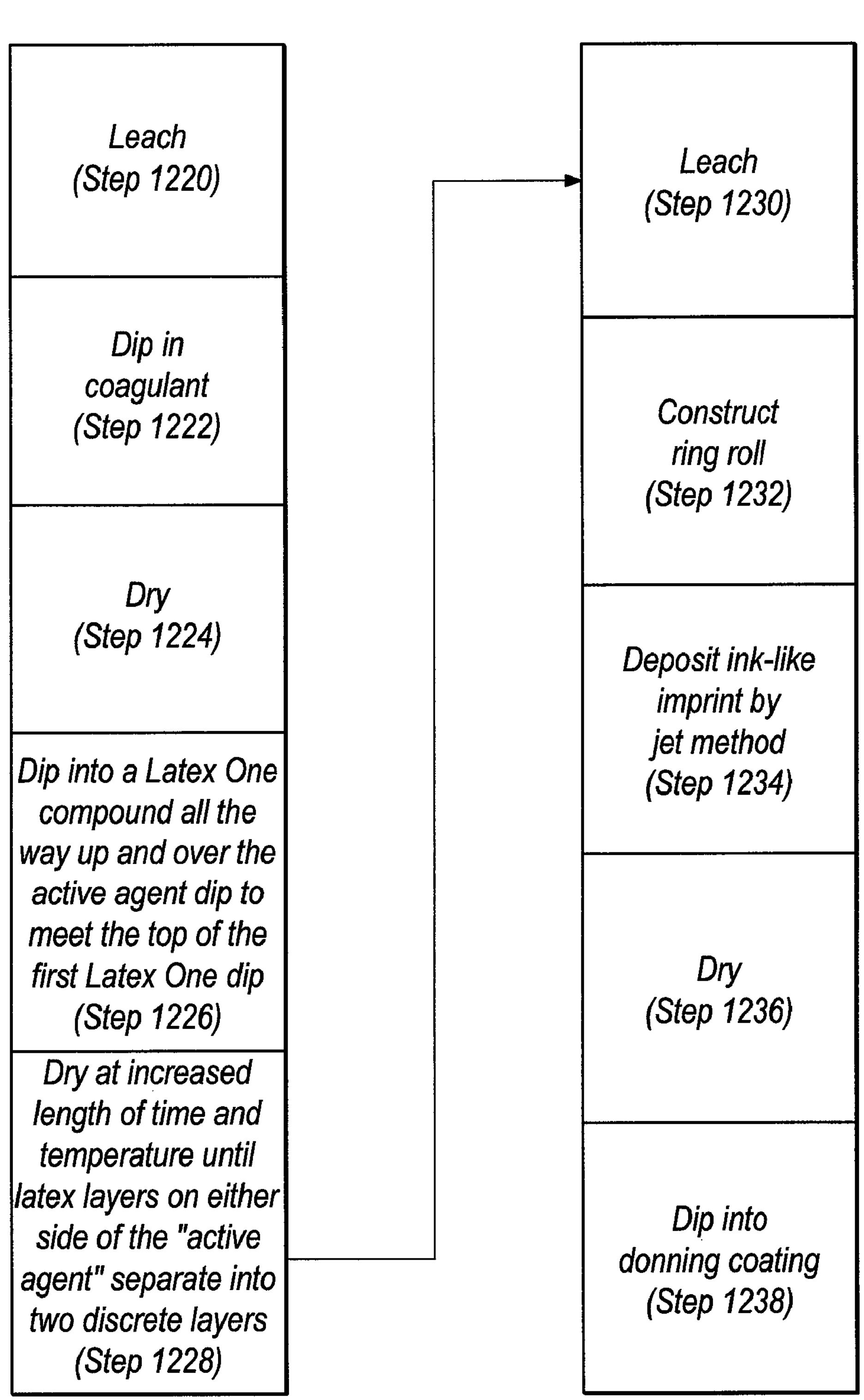

Method of Making Multi-Colored Membranes with One or More Discrete Layers, Including Imprint Features, and Dye Transfer (Tattoo) Features:

Referring now to FIGS. 12A-C, a process for making multi-colored membranes with one or more discrete layers, including an imprint feature and dye transfer (tattoo) feature is illustrated. Starting with FIG. 13A steps 1200, 1202, 1024, 1206, 1208, 1210, and 1212 mirror steps 1100, 1102, 1104, 1106, 1108, 1110, and 1112 described above.

With continued reference to FIG. 12A, the process continues at step 1214 with the interim product following steps 1200-1212, is dipped into a coagulant layer that also contains a separating agent, up to about three inches from the top of the present latex film—the top of the wrist. At step 1216 the interim product is then dipped into an active agent, also a purple dye, composed of, by weight, 1% crystal violet, 3% wax #09730 and 96% deionized water, over the present layer of Latex One but stopping approximately 3 inches short of the top to match exactly the portion of the previous dip of the coagulant and separation compound. The interim product is then dried until slightly tacky at step 1218.

Continuing on with FIG. 12B, the interim product is leached at step 1220 followed by another dip in coagulant at step 1222. At step 1224, the interim product is dried. At step 1126, the interim product is dipped into a Latex One compound all the way up and over the active agent dip to meet the top of the first Latex One dip. At step 1228, the interim product is dried at increased length of time and temperature until latex layers on either side of the "active agent" separate into two discrete layers.

Continuing on with FIGS. 12B and 12C, steps 1230, 1232, 1234, 1236, 1238, 1240, 1242, 1244, 1246 mirror steps 1130, 1132, 1134, 1136, 1138, 1140, 1142, 1144, and 1146 described above in relating to FIGS. 12B-12C. The resultant product, at step 1248, is a membrane product with one or more discrete layers.

It is appreciated that the "discrete separating" steps may be repeated to produce any desired number of discrete layers of any elastomer, in any thicknesses and may or may not contain "active agents" in the elastomer compound. Discretely separated layers may also be constructed as to separate enough to offer an additional feature of a substance between the separated layers which act as a reservoir for such substance as, for example, membrane product 300, FIG. 3; membrane product 600, FIG. 6; membrane product 700, FIG. 7; and membrane product 800, FIG. 8.

This glove may or may not have an imprint. If the glove is to be inverted when it is stripped, the imprint step should take place after Step 1208 above and positioned so that when glove is inverted the symbols reads or shows itself properly.

The process may also, using separating agents, produce any number of discrete colored layers and some discrete enough as to form reservoir areas into which additional substances can be deposited during the dipping process. A variety of different potential separating agents may be employed, including: zinc stearates and other stearates, hydrogel compositions, powders such as calcium carbonates, cornstarch, microspheres, wax emulsions such as paraffin and micro-crystalline, silicon emulsions, gentian violet at high concentrations, silicon oils, acrylic separating compositions, separate curing of latex layers, and chlorination of the first latex layer before application of the second layers. And reservoirs include different substances including, but not limited to, gels, biocides, chemicals, silicones, neutralizing chemicals, buffering chemicals, spermicides, lubricants, tactile enhancers, and other materials for inhibiting penetration or providing treatment of needles and other sharps. It should be appreciated that this double-membrane configuration can also be made by the above method with a biocide acting as a coagulant component, which in certain concentrations can also act as a separating agent. It can be employed by dipping in biocide before dipping in the coagulant, or by mixing the biocide or chemical with the coagulant. Other methods of making a multi-layer latex membrane known in the art, such as a method using a coagulant with or without a separating agent as disclosed in U.S. Pat. No. 5,679,399, the entire disclosure of which is hereby incorporated by reference herein.

The formation of the second layer requires flexibility in regard to dipping speeds depending upon the particular formulations of latex, separating agent, and coagulants employed. For example, different dipping speeds may be employed in the cuff region (not coated with the separating agent) and the main body region, and/or the second layer may be double dipped in the main region and single dipped in the cuff region.

As an alternative to dip or spray forming of multi-colored latex, synthetic, or polymer membranes having multiple discrete layer, colorations and actives, the techniques described above may also be employed in connection with conventional sheet forming and extrusion processes to make a variety of other multiple layer membranes. For example, a multiple layer medical or other type of tubing may be formed using an extrusion process. As in the case of dip or spray forming techniques, the various layers of multiple layer membranes formed by sheeting or extrusion techniques may be joined or fused in selected regions and separated or discrete in other selected regions. Such multiple layer membranes find applications in products such as catheters and or products where an added measure of security against rupture is desired, for example in colostomy bags.

Active agents such as biocides may be more effectively picked up and retained by certain polymer films.

Additionally, the biocides may be introduced on, and/or into the polymer during the fabrication of the film in such a way as to be available to provide disinfectant properties. This can be accomplished by conventional dipping or mixing, with additional layers deposited by dipping, casting, spray coating, vacuum depositing, passing through fluidized beds, centrifugal spinning, etc. Outer coats can be formed by similar techniques to contain the biocide and minimize leaching where desirable.

Coatings within the scope of the present invention include spermicides such as Nonoxinol-9 and one or more organopolysiloxane compounds which may be applied to latex membranes as disclosed in U.S. Pat. No. 5,304,375, the entire disclosure of which is hereby incorporated by reference herein. Rubber membranes may be provided with a transparent coating of an aqueous composition containing a preformed latex binder, an emulsifying agent, an inorganic fluoro-containing compound, and a thickening agent as described in U.S. Pat. No. 5,182,142, the entire disclosure of which is hereby incorporated by reference herein. A cellulosic coating material including synthetic latex formed by emulsification of cellulosic polymers stabilized by surfactants and containing a water-soluble pore forming agent and a plasticizer may also be employed, as described in U.S. Pat. No. 5,126,146, the entire disclosure of which is hereby incorporated by reference herein.

Additionally, the biocides may be incorporated into porous and non-porous polyurethane films, as described in more detail in U.S. Pat. No. 5,679,699, incorporated by reference herein in its entirety. In brief, biocides may be introduced 1) by physical entrapment in the pores of a porous film during fabrication of the film or subsequent to the fabrication of the film, 2) adsorption of the biocide on internal pore surface, 3) precipitation of the biocide within a rubber matrix (method applicable to non-porous urethane films), and 4) chemical bonding of the biocide to functional groups on polyurethane chains (method applicable to both porous and nonporous films). Temperatures, speeds, and dwell times may also vary dependent upon the particular formulations employed. In the case of both latex and polymer or synthetic membranes, the first and second layers and following layers may be selectively fused or separated by selective application and/or variations in the formulation of the polymer, separating agent, coagulant, surfactant and or active agent.

While nitrile and vinyl gloves come from synthetic materials, unlike latex made from natural rubber, it will be appreciated that the manufacturing process for the synthetic materials is similar to latex glove production and one of ordinary skill in the art would understand how to adjust the processes described herein to accommodate the synthetic polymer materials. Furthermore, while the processes are described primarily in terms of producing a membrane product in the form of a glove, other forms for producing other membrane products, including other products mentioned in this application, will occur to one of ordinary skill in the art.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

It will be appreciated that the term membrane product extends well beyond medical gloves and condoms. For example, the features described herein may also extend to membrane and elastomer products such as, but not limited to: diaphragms, dressings, sheaths, slippers, overshoes, bands, catheters, tubing, drapes, gut openings, mouth pieces, baby nipples, intra gastric nasal tubes, tubes, shunts, dental dams, dams and colostomy products and other bags.

Certain numerical ranges, capacities, and ratios have been mentioned in this description but are meant to be exemplary in nature and non-limiting. As one example, the temperature preferences set forth in the processes described herein are listed is 50-60 Celsius, (equating to approximately 120-140 degrees Fahrenheit), 54 degrees Celsius (equating to approximately 129 degrees Fahrenheit), and 65 degrees Celsius (equating to approximately 149 degrees Fahrenheit). However, other suitable ranges may be used as well, including those found in U.S. Pat. Nos. 4,771,482; 4,919,966; 4,935,260; 5,045,341; 5,128,168; 5,130,159; 5,165,593; 5,338,565; 5,549,924; 5,679,399; and 5,965,276, all to Shlenker, some of which include a range of 210-220 degrees Fahrenheit for heating the glove former for example, and which are all incorporated by reference herein. Other suitable temperature ranges will occur to one of ordinary skill in the art familiar with membrane glove manufacturing.

Certain objects and advantages of the invention are described herein. Of course, it is to be understood that not necessarily all such objects or advantages may be achieved in accordance with any particular embodiment of the invention. Thus, for example, those skilled in the art will recognized that the invention may be embodied or carried out in a manner that achieves or optimizes one advantage or group of advantages as taught herein without necessarily achieving other objects or advantages as may be taught or suggested herein.

It is also contemplated that various combinations or sub-combinations of the specific features and aspects of the embodiments may be made and still fall within the scope of the invention. Accordingly, it should be understood that various features and aspects of the disclosed embodiments may be combined with or substituted for one another in order to form varying modes of the disclosed invention. Thus, it is intended that the scope of the present invention herein disclosed should not be limited by the particular disclosed embodiments described above.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. In addition, while a number of variations of the invention have been shown and described in detail, other modifications, which are within the scope of this invention, will be readily apparent to those of skill in the art based upon this disclosure.

What is claimed is:

1. A safety barrier for protecting an underlying surface from exposure to pathogens, the barrier comprising:

a membrane having a form configured to fit closely over at least a portion of the underlying surface, the membrane having an outermost surface disposed distalmost from the underlying surface when the membrane is placed thereon, the membrane further including at least one protected region with at least a portion of the at least one protected region having one or more built-in safety features configured to inhibit the exposure to pathogens onto or into the underlying surface with at least one of the one or more built-in safety features being defined by a set of safety-related properties including a presence, a location, and a prevention type; and at least one safety indicator carried by the membrane and providing a visually-perceptible alert at the outermost surface of the membrane, the visually-perceptible alert indicative of at least one safety-related property of the at least one safety feature, wherein the visually-perceptible alert is visually perceptible prior to a breach of the outermost surface of the membrane.

2. The safety barrier of claim 1, wherein the safety-related properties further include a substance identifier, wherein the substance identifier indicates a type of substance included in the membrane.

3. The safety barrier of claim 1, wherein the at least one of the one or more built-in safety features is a variation in hardness in the at least one protected region of the membrane.

4. The safety barrier of claim 1, wherein the visually-perceptible alert is located exclusively on the outermost surface of the membrane in both an unprotected region and the protected region.

5. The safety barrier of claim 1, wherein the visually-perceptible alert is located exclusively on the outermost surface of the membrane within an unprotected region.

6. The safety barrier of claim 1, wherein the visually-perceptible alert is indicative of the presence, a specific location, and a specific prevention type of the at least one of the one or more built-in safety features in the protected region.

7. The safety barrier of claim 1, wherein the visually-perceptible alert is indicative of the presence and a specific location of the at least one of the one or more built-in safety features in the protected region.

8. The safety barrier of claim 1, wherein the at least one of the one or more built-in safety features is a variation in thickness in the at least one protected region of the membrane.

9. The safety barrier of claim 1, wherein the membrane includes a single layer.

10. The safety barrier of claim 1, wherein the membrane includes multiple layers.

11. The safety barrier of claim 10, wherein the multiple layers are bonded together to from a unitary layer.

12. The safety barrier of claim 10, wherein at least two of the multiple layers are discrete and not joined together in at least one location.

13. The safety barrier of claim 12, wherein at least one reservoir is disposed between adjacent layers of the at least two of the multiple layers.

14. The safety barrier of claim 13, wherein the at least one reservoir is at least partially filled with an active agent.

15. The safety barrier of claim 1, wherein the visually-perceptible alert is indicative of the presence of the at least one built-in safety feature in the protected region.

16. The safety barrier of claim 1, wherein the visually-perceptible alert is indicative of the general location of the at least one built-in safety feature in the protected region.

17. The safety barrier of claim 1, wherein the visually-perceptible alert is indicative of the specific location of the at least one built-in safety feature in the protected region.

18. The safety barrier of claim 1, wherein the visually-perceptible alert is indicative of the general prevention type of the at least one built-in safety feature in the protected region.

19. The safety barrier of claim 1, wherein the visually-perceptible alert is indicative of the specific prevention type of the at least one built-in safety feature in the protected region.

20. The safety barrier of claim 1, wherein the visually-perceptible alert is indicative of the presence, general location, and general prevention type of the at least one built-in safety feature in the protected region.

21. The safety barrier of claim 1, wherein the visually-perceptible alert is indicative of the presence, specific location, and specific prevention type of the at least one built-in safety feature in the protected region.

22. The safety barrier of claim 1, wherein the visually perceptible alert is indicative of the presence and general location of the at least one built-in safety feature in the protected region.

23. The safety barrier of claim 1, wherein the visually-perceptible alert is indicative of the presence and specific location of the at least one built-in safety feature in the protected region.

24. The safety barrier in claim 1, further comprising:

a second protected region having at least one fewer built-in safety feature than the first protected region.

25. The safety barrier of claim 1, wherein the visually-perceptible alert includes a first color in the protected region having an active agent and a second contrasting color in an unprotected region or passively protected region, wherein the second color is different from the first color.

26. The safety barrier of claim 1, wherein the visually-perceptible alert includes a first color tone in the protected region and a second color tone in an unprotected region, wherein the second color tone is different from the first color tone.

27. The safety barrier of claim 1, wherein the visually-perceptible alert includes a first indicia in the protected region and a second indicia in an unprotected region.

28. The safety barrier of claim 1, wherein the visually-perceptible alert includes a first pattern in the protected region and a second pattern in an unprotected region.

29. The safety barrier of claim 1, wherein the visually-perceptible alert includes an indicia.

30. The safety barrier of claim 1, wherein the visually-perceptible alert comprises a number.

31. The safety barrier of claim 1, wherein the visually-perceptible alert includes a pattern.

32. The safety barrier of claim 1, wherein the visually-perceptible alert includes at least one line of demarcation.

33. The safety barrier of claim 1, wherein the visually-perceptible alert includes at least one zone of demarcation.

34. The safety barrier of claim 1, wherein the form of the membrane is a glove with a finger region, a palm region, and a cuff region.

35. The safety barrier of claim 34, wherein the protected region is disposed within the finger region of the glove.

36. The safety barrier of claim 34, wherein the protected region is disposed within the palm region of the glove.

37. The safety barrier of claim 34, wherein the protected region is disposed within the cuff region of the glove.

38. The safety barrier of claim 34, wherein the protected region is disposed within the finger and palm regions of the glove.

39. The safety barrier of claim 34, wherein the protected region extends into the finger, palm, and cuff regions of the glove.

40. The safety barrier of claim 1, wherein the form of the membrane is a condom.

41. The safety barrier of claim 1, wherein the underlying surface is an epidermal surface.

42. The safety barrier of claim 1, wherein the membrane includes a plurality of protected regions.

43. The safety barrier of claim 1, wherein the presence in the set of safety-related properties indicates that the at least one built-in safety feature is included in the membrane.

44. The safety barrier of claim 1, wherein the location in the set of safety-related properties indicates the general or specific location in the membrane of the at least one built-in safety feature.

45. The safety barrier of claim 1, wherein the prevention type in the set of safety-related properties indicates the type of prevention available in the membrane of the at least one built-in safety feature.

46. The safety barrier of claim 1, wherein the safety-related properties further include a substance identifier.

47. The safety barrier of claim 46, wherein the substance identifier in the set of safety-related properties indicates the type of substance included in the membrane.

48. The safety barrier of claim 1, wherein the at least one built-in safety feature is a plurality of layers in the protected region of the membrane.

49. The safety barrier of claim 1, wherein the at least one built-in safety feature is a variation of toughness in the protected region of the membrane.

50. The safety barrier of claim 1, wherein the at least one built-in safety feature is an active agent in the protected region of the membrane.

51. The safety barrier of claim 1, wherein the at least one built-in safety feature is a biocide in the protected region of the membrane.

52. The safety barrier of claim 1, wherein the at least one built-in safety feature is an anti-microbial substance in the protected region of the membrane.

53. The safety barrier of claim 1, wherein the at least one built-in safety feature is a pigment selected to adhere to a sharp object passing completely through an innermost surface of the membrane in the protected region and place a mark the underlying surface indicative of contact between the sharp object and the underlying surface.

54. The safety barrier of claim 53, wherein the pigment is a dry substance selected from the list consisting of: a powder, a flake, a granule, and a crystal.

55. The safety barrier of claim 53, wherein the pigment is configured to place a semi-permanent or permanent mark on the underlying surface when the sharp object comes into contact with the underlying surface.

56. The safety barrier of claim 53, wherein the pigment is configured to place a temporary mark on the underlying surface when the sharp object comes into contact with the underlying surface.

57. The safety barrier of claim 53, further comprising:

a carrier solution encapsulating the pigment.

58. The safety barrier of claim 53, wherein the pigment is impregnated into the membrane.

59. The safety barrier of claim 53, wherein the pigment is disposed within one or more reservoirs between adjacent layers of the membrane in the protected region.

60. The safety barrier of claim 1, wherein the visually perceptible alert is entirely on the outermost surface of the membrane in both an unprotected region and in the protected region.

61. The safety barrier of claim 1, wherein the visually perceptible alert is entirely on the outermost surface of the membrane within an unprotected region.

62. The safety barrier of claim 1, wherein the visually perceptible alert is entirely on the outermost surface of the membrane within the protected region.

63. The safety barrier of claim 1, wherein the visually-perceptible alert comprises a symbol.

64. The safety barrier of claim 1, wherein the visually-perceptible alert comprises a character.

65. The safety barrier of claim 1, wherein, the visually-perceptible alert comprises one or more word.

66. The safety barrier of claim 1, wherein the visually-perceptible alert comprises a descriptor.

67. The safety barrier of claim 1, wherein the visually-perceptible alert comprises a design.

68. The safety barrier of claim 1, wherein the visually-perceptible alert comprises a stripe.

69. The safety barrier of claim 68, wherein the visually-perceptible alert comprises a double stripe.

70. The safety barrier of claim 1, wherein the membrane comprises an elastomer.

71. The safety barrier of claim 70, wherein the membrane comprises latex.

72. The safety barrier of claim 70, wherein the membrane comprises nitrile rubber.

73. A safety barrier for protecting an underlying surface from exposure to pathogens, the barrier comprising:

a membrane having a form configured to fit closely over at least a portion of the underlying surface, the membrane having an outermost surface disposed distalmost from the underlying surface when the membrane is placed thereon, the membrane further including at least one protected region with at least a portion of the at least one protected region having one or more built-in safety features configured to inhibit the exposure to pathogens onto or into the underlying surface with at least one of the one or more built-in safety features being defined by one or more safety-related properties selected from the list consisting of: a presence, a location, and a prevention type, the membrane comprising a safety indicator providing a visually-perceptible alert at the outermost surface of the membrane, the visually-perceptible alert indicative of at least one safety-related property of the at least one safety feature, wherein the visually-perceptible alert is visually perceptible prior to a breach of the outermost surface of the membrane.

* * * * *